US009173778B2

(12) United States Patent
Schoelling

(10) Patent No.: US 9,173,778 B2
(45) Date of Patent: *Nov. 3, 2015

(54) TAMPON HAVING SPIRALLY SHAPED GROOVES

(75) Inventor: Hans Werner Schoelling, Ennepetal (DE)

(73) Assignee: EVEREADY BATTERY COMPANY, INC, St. Louis, MO (US)

(*) Notice: Subject to any disclaimer, the term of this patent is extended or adjusted under 35 U.S.C. 154(b) by 663 days.

This patent is subject to a terminal disclaimer.

(21) Appl. No.: 10/104,264

(22) Filed: Mar. 22, 2002

(65) Prior Publication Data

US 2002/0151859 A1 Oct. 17, 2002

(30) Foreign Application Priority Data

Mar. 26, 2001 (DE) .................................. 101 14 786

(51) Int. Cl.
A61F 13/15 (2006.01)
A61F 13/20 (2006.01)

(52) U.S. Cl.
CPC .................................. A61F 13/2051 (2013.01)

(58) Field of Classification Search
USPC ............... 604/904, 385.17, 380–381; 28/118, 28/119, 123, 125
See application file for complete search history.

(56) References Cited

U.S. PATENT DOCUMENTS 2,099,931 A * 11/1937 Fourness ....................... 604/364
2,798,260 A 7/1957 Niepmann et al.
2,815,756 A 12/1957 Graham, Jr.
2,965,101 A * 12/1960 Schirmer et al. .......... 604/385.18
3,011,495 A * 12/1961 Brecht .......................... 604/377
3,063,453 A * 11/1962 Brecht .......................... 604/377
3,422,496 A 1/1969 Wolff et al.
3,508,548 A * 4/1970 Messing et al. ............... 604/375
3,618,605 A 11/1971 Glassman
3,854,481 A 12/1974 Messing
4,175,561 A * 11/1979 Hirschman ............... 604/385.17
4,328,804 A 5/1982 Shimatani
4,351,339 A 9/1982 Sneider
4,627,849 A * 12/1986 Walton et al. ................. 604/379
4,707,318 A 11/1987 Can
4,755,166 A * 7/1988 Olmstead ........................ 604/11
4,816,100 A 3/1989 Friese (Continued)

FOREIGN PATENT DOCUMENTS

DE 2941306 A 11/1979
DE 3934153 A1 * 4/1991

(Continued)

OTHER PUBLICATIONS

Definition of "stable", Merriam Webster OnLine.*

(Continued)

Primary Examiner — Tatyana Zalukaeva
Assistant Examiner — Ginger T Chapman
(74) Attorney, Agent, or Firm — Edgewell Personal Care Brands, LLLC

(57) ABSTRACT

A tampon for feminine hygiene, having an insertion end, a recovery end, a recovery tape, and a longitudinal axis. The tampon is made of compressed fibrous material and has an outer surface that is at least partially provided with spirally shaped, pressed longitudinal grooves. The grooves define spirally shaped longitudinal ribs. Also disclosed is a method for producing the tampon.

32 Claims, 14 Drawing Sheets

(56) References Cited

U.S. PATENT DOCUMENTS

| | | | |
|---|---|---|---|
| 5,458,835 A | 10/1995 | Wilkes et al. | |
| 5,592,725 A * | 1/1997 | Brinker | 28/118 |
| 5,813,102 A | 9/1998 | Leutwyler et al. | |
| 5,832,576 A | 11/1998 | Leutwyler et al. | |
| 5,911,712 A | 6/1999 | Leutwyler et al. | |
| 6,283,952 B1 | 9/2001 | Child et al. | |
| 6,310,269 B1 * | 10/2001 | Friese et al. | 604/379 |
| 6,433,246 B1 | 8/2002 | Nguyen et al. | |
| D477,075 S * | 7/2003 | Schoelling | D24/125 |
| 6,939,340 B1 | 9/2005 | Berges | |
| 7,070,585 B2 | 7/2006 | Jensen | |
| 7,833,210 B2 * | 11/2010 | Schoelling | 604/385.17 |
| 7,967,803 B2 * | 6/2011 | Van Ingelgem et al. | 604/385.17 |
| 8,353,890 B2 | 1/2013 | Schoelling | |
| 2002/0157222 A1 | 10/2002 | Friese et al. | |
| 2003/0167048 A1 | 9/2003 | Policappelli | |

FOREIGN PATENT DOCUMENTS

| | | | | |
|---|---|---|---|---|
| DE | 197 47 633 C | | 3/1999 | |
| EP | 422660 A1 | * | 4/1991 | A61F 13/20 |
| EP | 0 465 502 B | | 1/1992 | |
| EP | 0 597 446 A | | 5/1994 | |
| EP | 693363 A1 | | 1/1996 | |
| EP | 1481656 A1 | * | 12/2004 | A61F 13/20 |
| GB | 113275 A | | 10/1918 | |
| GB | 811 756 A | | 4/1959 | |
| GB | 1082770 | * | 9/1967 | A61I 15/10 |
| GB | 1280499 A | | 7/1972 | |
| GB | 2032783 A | | 10/1978 | |
| WO | WO 00/53141 A1 | | 9/2000 | |
| WO | WO 0053141 | * | 9/2000 | A61F 13/20 |

OTHER PUBLICATIONS

PCT Search Report for PCT/EP02/03263 dated Feb. 27, 2003.
PCT Search Report for PCT/EP02/03262 dated Feb. 28, 2003.

* cited by examiner

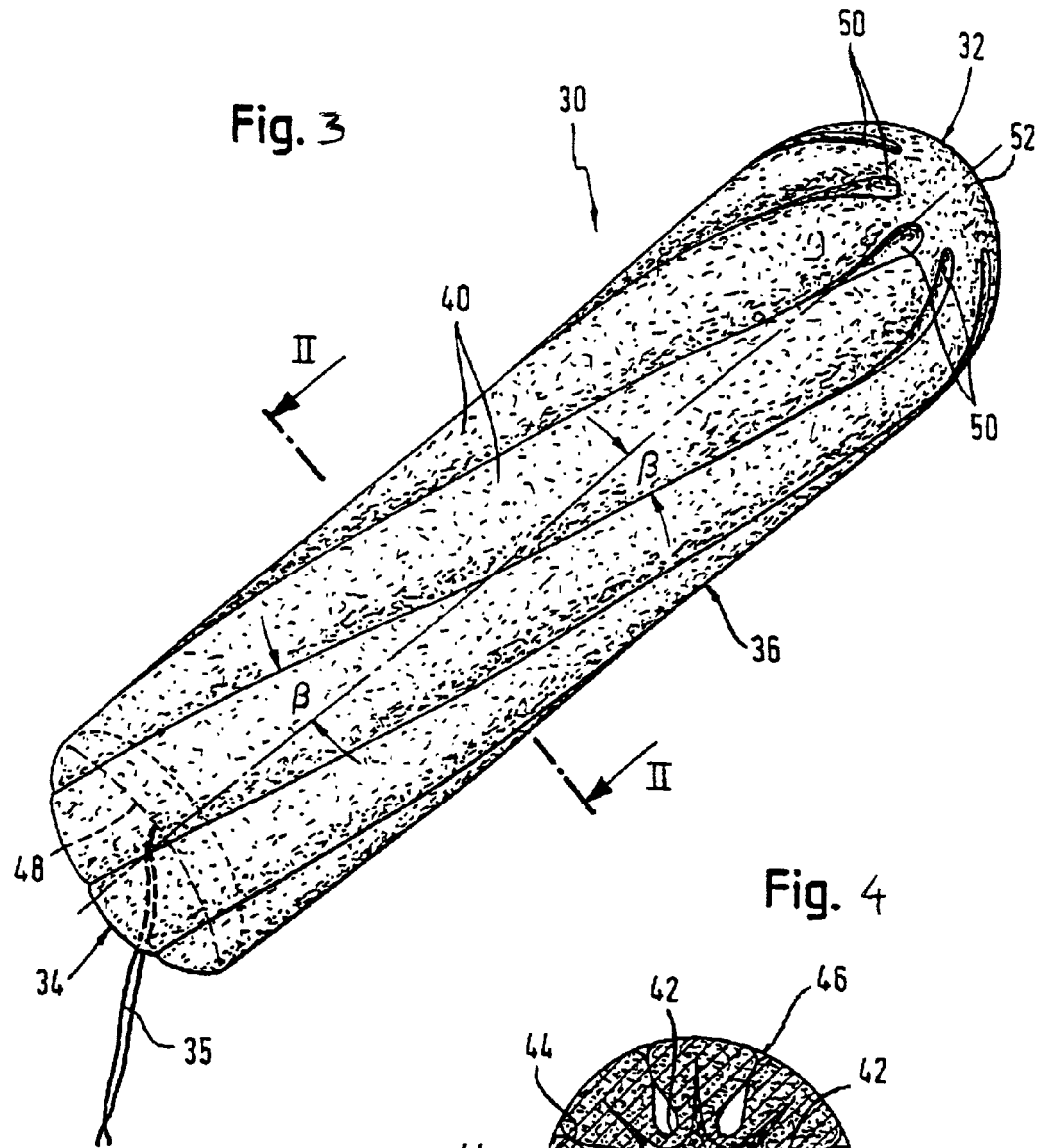
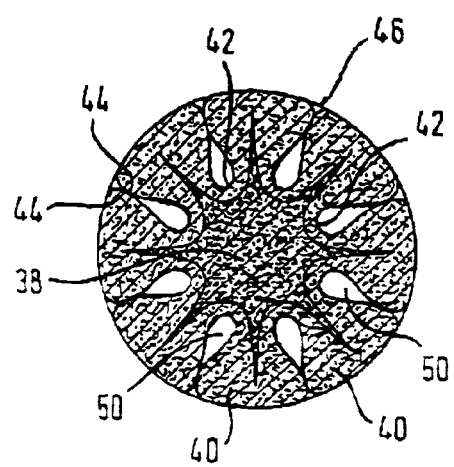

TAMPON HAVING SPIRALLY SHAPED GROOVES

This application claims priority of German Patent Application No. 10114786.4-45, filed Mar. 26, 2001, the disclosure of which is herein incorporated by reference.

FIELD OF THE INVENTION

The invention relates to a tampon for feminine hygiene having pressed, spiral grooves.

BACKGROUND OF THE INVENTION

State of the art tampons and methods and equipment for their manufacture are disclosed in Leutwyler, et al., U.S. Pat. Nos. 5,911,712, 5,813,102, and 5,832,576. The tampon has an insertion end, a recovery end with a recovery tape, and a central section extending between the insertion end and the recovery end. It has a compressed, generally cylindrical, solid fibrous core, from which relatively uncompressed longitudinal ribs extend radially outward. Each rib is separated from adjacent ribs in the vicinity of the compressed fiber core to an extent which is greater than that extent to which such a rib is separated from an adjacent rib remotely from the compressed fiber core. Further, the fiber core can be pressed more strongly in the central area than in the area of the recovery end of the tampon. The recovery end of the tampon can also be provided with a finger recess and the insertion end with a round dome. Finally, the tampon is at least partially surrounded by a liquid-permeable sheathing.

Such a tampon can be formed with the following steps: rolling up a length of a continuous fibrous web to form a generally cylindrical tampon blank with a circumferential surface; simultaneous radial pressing of narrow, strip-shaped sections of the circumferential surface of the tampon blank arranged in a spaced manner to form a number of longitudinal grooves which are separated from one another by relatively uncompressed longitudinal ribs which extend radially outward from a relatively compressed core, the core being compressed to a smaller extent in the area of the recovery end of the tampon than in its remaining area; and pressing of outer ends of the longitudinal ribs radially inward to form a soft, smooth circumferential surface, while the relatively uncompressed fibrous structure of the ribs is preserved. Furthermore, a finger recess and a round dome can be provided at the recovery end and the insertion end of the tampon respectively. Lastly, a liquid-permeable sheathing is fixed on the fibrous web at least in parts, so as to provide a liquid-permeable layer on at least part of the outer surface of the tampon blank.

The formation of the grooves and ribs of this state of the art tampon are known from these disclosures and that of Friese et al., U.S. Pat. No. 6,310,269, which provides a tampon, especially useful as a digital tampon, that has a densified central core and a softer outer surface.

While this tampon represents a significant improvement over the previously commercialized tampons, there remain areas susceptible to improvement. One such improvement that is desirable is increased surface area to reduce the likelihood of early leakage of fluids flowing down the surface of the tampon.

Patent literature has also suggested that coiled tampons can be formed for improved flexibility (such as disclosed in Brecht, U.S. Pat. No. 3,011,495, and Schirmer et al., U.S. Pat. No. 2,965,101) and for easier withdrawal (such as disclosed in Shimatani, U.S. Pat. No. 4,328,804, and Sneider, U.S. Pat. No. 4,351,339). These coiled tampons are generally formed by twisting one or more "ropes" of material. However, these improvements in flexibility and withdrawal characteristics appear to result in reduced column strength.

The object of the invention is to improve the tampon, the method and the apparatus as described above in such a manner that the risk of leakage after the tampon has been put into use is reduced considerably by extending the time over which the tampon absorbs body fluid, and by enlarging the surface of the tampon and increasing the fiber quantity available for immediate absorption of body fluid after the introduction of the tampon, in particularly preferred embodiments in the area of the fiber core.

SUMMARY OF THE INVENTION

The invention achieves this object by virtue of a tampon for feminine hygiene having an insertion end, a recovery end, and a longitudinal axis. The tampon is made of compressed fibrous material having an outer surface. The outer surface of the tampon is at least partially provided with spirally shaped, pressed longitudinal grooves. The tampon is preferably compressed radially with respect to the longitudinal axis. It can have an essentially uniform density over a cross-section of the tampon, or it can have a core of highly compressed fibrous material from which core longitudinal ribs extend radially outward. The longitudinal ribs are thus defined by the spirally shaped, pressed longitudinal grooves.

As a result of the longer distances the body fluid has to cover on account of the spiral design of the longitudinal ribs and of the spiral longitudinal grooves extending between these along the surface of the tampon, and as a result of the associated longer dwell time of the liquid in the spiral longitudinal grooves, the absorption and expansion capacity of the tampon is utilized in a considerably better manner.

The invention also provides a method of producing a tampon. The method includes providing a tampon blank of tangled fibrous material; and compressing the tampon blank and at least partially forming spirally shaped longitudinal grooves at the outer surface of the tampon in order to enlarge the absorbent surface of the tampon. Preferably, the tampon blank is radially compressed with respect to the longitudinal axis on narrow lines of its circumferential surface. Again, the tampon blank can be compressed to provide an essentially uniform density over the cross-section of the tampon, or it can provide a core with a high degree of compression, from which relatively uncompressed longitudinal ribs extend radially outward.

One embodiment of the tampon of the present invention can be manufactured using an apparatus for producing a tampon. The apparatus has a press having press jaws of substantially equal dimensions which are arranged in a star formation with respect to the press axis. The jaws can be moved synchronously in a common plane radially with respect to the press axis between their open position and closed position. In their closed position, the jaws can support one another on their mutually opposite longitudinal sides. Each press jaw has a stepped pressing surface wherein the pressing surfaces of the press jaws preferably form a press opening of round cross section with a length in the range from 40 to 70 mm. In addition, each pressing surface has a pressing blade, which is oriented toward the press opening, and a pressing shoulder, which is arranged only on a specific side flank of the pressing blade and in each case is oriented in the same circumferential direction about the press axis. The pressing shoulder is offset to the outside in relation to the press axis with respect to a pressing edge at the free, inner end of the pressing blade, and the area of the pressing shoulder is greater than the pressing edge of the pressing blade of each press jaw. The pressing surface, including the pressing blade and the pressing shoulder, is spirally shaped.

BRIEF DESCRIPTION OF THE DRAWING

The invention is described in greater detail below with reference to the diagrammatic drawing of illustrative embodiments of the tampon and of the apparatus for implementing the method of producing the tampon, in which:

FIG. 3 shows a tampon with spiral longitudinal ribs and longitudinal grooves according to another embodiment of the invention in a perspective illustration;

FIG. 4 shows a cross section of the tampon in FIG. 2 along the line II-II;

DETAILED DESCRIPTION OF THE INVENTION

Figure 1:
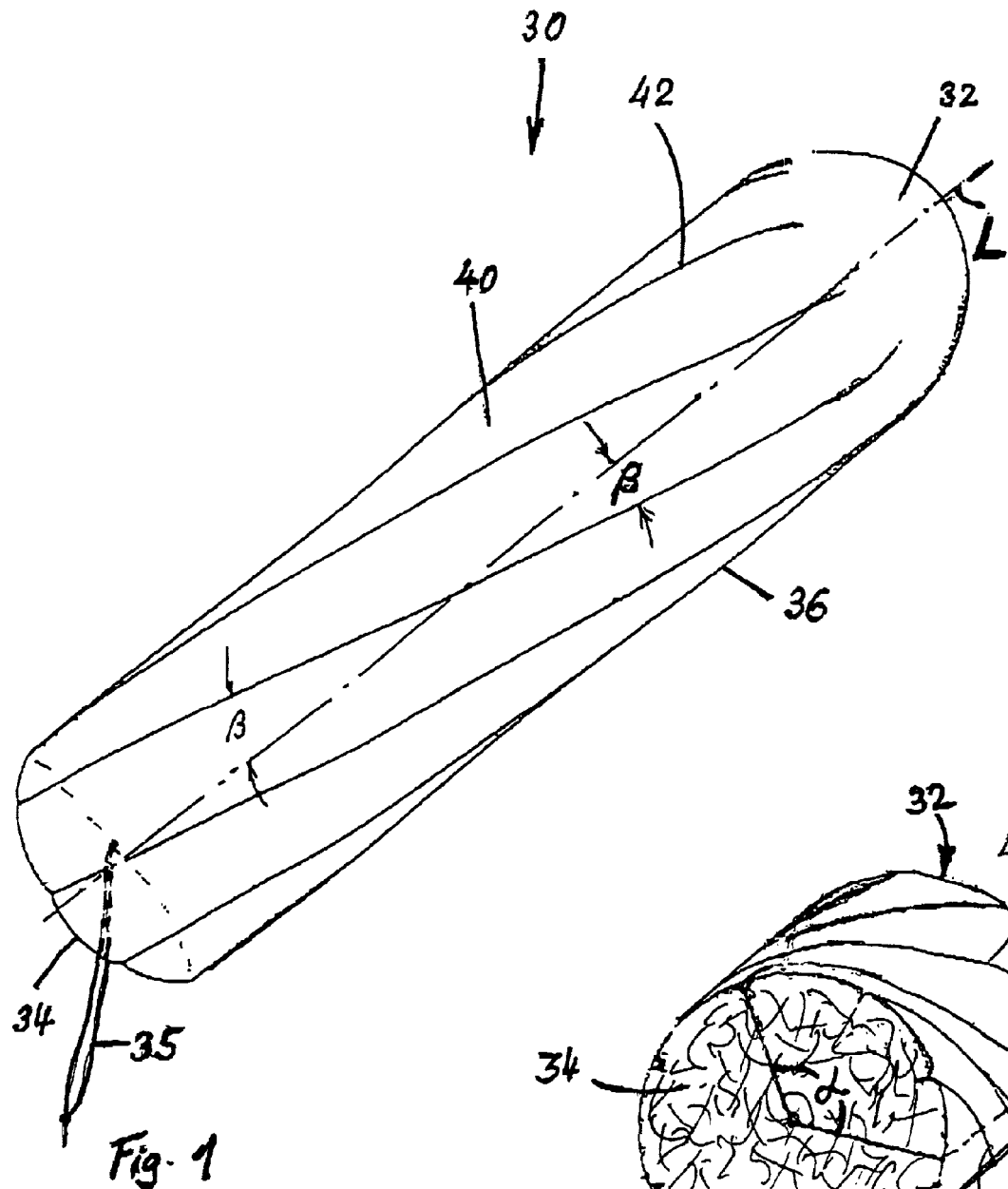
FIG. 1 shows a tampon with spiral longitudinal ribs and longitudinal grooves according to the invention in a perspective illustration.

According to one embodiment of the present invention, FIG. 1 illustrates a tampon 30 for feminine hygiene, having an insertion end 32, a recovery end 34, a longitudinal section 36 having a longitudinal axis L and lying therebetween, and a flexible recovery element, such as a recovery tape 35. The tampon 30 preferably consists of a radially compressed fibrous material.

The outer surface of the tampon 30 is at least partially provided with longitudinal ribs 40 defined by pressed longitudinal grooves 42. The longitudinal ribs 40 are spirally or helically shaped in the axial direction between the insertion end 32 and the recovery end 34 and preferably extend over at least about 80° of the tampon circumference. However, the circumferential angle α can, depending also on the dimensions of the tampon, be selected in the range of up to at least 150°, preferably in the range of 80° to 120° of the tampon 30. The number of longitudinal ribs 40 can vary, for example depending on the diameter of the tampon and/or the type of absorption material. Preferably, there are at least about four ribs, and more preferably, at least about six. While the present invention, like many known tampons, my have an even number of ribs, it is also possible to produce tampons according to the present invention with an odd number of ribs.

These tampons may be produced in accordance with the general teaching of Friese et al., U.S. Pat. No. 6,310,269, and Leutwyler et al., U.S. Pat. No. 5,832,576, the disclosures of which are herein incorporated by reference. These apparatus and methods disclosed in these references are modified, as described below, to form the tampons of the present invention. In addition, the tampons having pressed spiral grooves may also be produced in accordance with the general teaching of Neipmann et al., U.S. Pat. No. 2,798,260, and Wolff et al., U.S. Pat. No. 3,422,496, the disclosures of which are herein incorporated by reference. Again, these apparatus and methods disclosed in these references can be modified according to the general principles described below to form other embodiments of the tampons of the present invention. In particular, the individual press jaws and components can be formed in the spiral manner as described hereinbelow.

Figure 2:
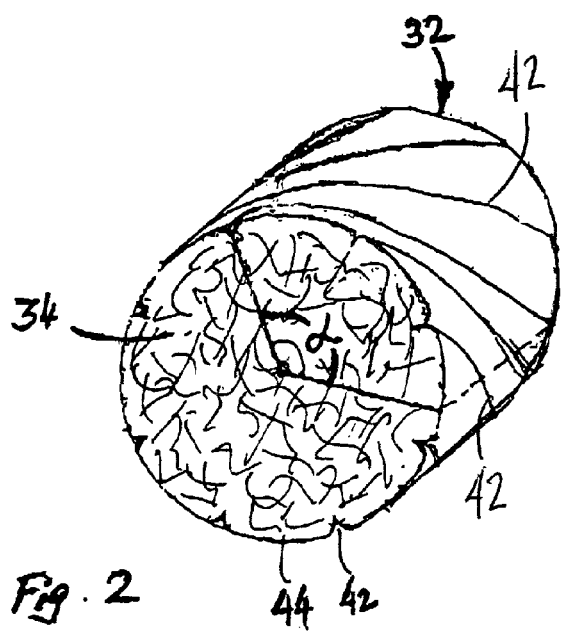
FIG. 2 shows the measurement of a circumferential angle α of a spiral longitudinal groove on a tampon according to the invention in a perspective illustration, taken from the rear end.

As shown in FIG. 2, the spiral longitudinal grooves 42 defining these ribs 40 can each extend over a circumferential angle α of up to at least 150° of the tampon. FIG. 2 also shows that the fibrous material of the tampon 30 can have an essentially uniform density over the cross section.

As mentioned above, the spiral grooves 42 enlarge the surface of the tampon and provide longer distances for the body fluid to traverse before leakage around the tampon occurs. This improvement can results from any depth of groove. However, it is preferred that the groove has a depth of at least about 1 mm. In the embodiment discussed below in regard to FIGS. 3 and 4, the groove may have a depth of more than about 4 mm, preferably about 4 mm to about 6 mm.

Preferably, the ribs are separated from adjacent ribs proximate the core to an extent which is greater than that extent to which such a spiral rib is separated from an adjacent spiral rib remotely from the core.

In the embodiment of FIGS. 3 and 4, the tampon 30 has a compressed, central, solid, generally cylindrical fiber core 38 with a high degree of compression, which ensures the stability or column strength of the tampon 30 during digital introduction of the tampon 30 into a body cavity. The longitudinal ribs 40 are relatively uncompressed and have, in particular on a circumferential surface 46 of the tampon 30, a soft fibrous structure. The longitudinal ribs 40 extend radially outward at equal circumferential angle intervals from this solid fiber core 38. As shown in FIG. 4, the spiral longitudinal ribs 40 are separated from one another by corresponding spiral longitudinal grooves 42 at least proximate the fiber core 38. According to a further embodiment of the invention, however, the circumferential surface of the tampon and its fiber core can also be substantially cylindrical with a circular cross-section, or even an oval cross-section.

In a more preferred embodiment, the longitudinal grooves 42 are closed, at least at the circumferential surface 46 of the tampon 30, as the side flanks 44 of adjacent longitudinal ribs 40 touch one another to form the soft, closed circumferential surface 46 of the tampon 30. This circumferential surface 46 of the tampon 30 makes possible more gentle and therefore more pleasant introduction of the tampon 30 into the body cavity and a high absorption capacity of the same.

As a result of the fact that the outer ends lying against one another of the side flanks 44 of adjacent longitudinal ribs 40 close the longitudinal grooves 42 only at the circumferential surface 46 of the tampon 30, the longitudinal grooves 42 form in each case eight closed spiral guide ducts 50 (FIG. 4) which are in each case preferably open only at the insertion end 32 and at the recovery end 34 (the openings at the insertion end 32 are visible in FIG. 3). These guide ducts 50 each have a drop-shaped cross section which is largest at the fiber core 38 and tapers radially outwardly to the place in which the adjacent longitudinal ribs 40 lie against one another with the radially outer ends of their side flanks 44. Immediately after the introduction of the tampon 30 into the body cavity, these spiral guide ducts 50 convey the body fluid to the fiber core 38 also, in order to utilize its fibrous material immediately to increase the absorption capacity and expansion capacity of the tampon 30 and to accelerate the opening of the closed guide ducts 50 radially outwardly. Therefore, the arrangement of the spiral longitudinal ribs 40 and the spiral guide ducts 50 or longitudinal grooves 42 brings about an enlargement of the surface of the tampon 30 and consequently an extension of the dwell time or absorption time for body fluid, which results in the absorption capacity and expansion capacity of the fiber core 38 being improved considerably. At the same time, a reduction in the weight of fibrous material used in the tampon 30 is thus possible, which allows more economical production of the tampon 30.

The recovery end 34 of the tampon 30 is, as is known per se, provided with a finger recess 48, which facilitates the insertion of a finger to expand the recovery end 34 and to subsequently introduce the tampon 30 and accelerates the expansion of the tampon 30. For this purpose, the insertion end 32 of the tampon 30 also has a round dome 52, the outer edge of which is smoothed or chamfered. As the approximately hemispherical dome 52 has a relatively short length, the spiral longitudinal ribs 40 and spiral longitudinal grooves 42 can extend over an optimum length of the tampon 30.

The tampon 30 has an approximately circular diameter in the range from 6 to 17 mm, the compressed, approximately cylindrical fiber core 38 having a diameter of up to 5 mm. The tampon 30 is preferably at least partially surrounded by a liquid-permeable sheathing, which is known per se and therefore not shown. An example of this is disclosed in Friese, U.S. Pat. No. 4,816,100, the disclosure of which is herein incorporated by reference. This sheathing can consist of, for example, an airlaid nonwoven covering material made of tangled, at least in part thermoplastic, heat-sealing fibers or of a perforated plastic film (such as a three-dimensional apertured film), or the like. In particular when nonwoven covering material is used for the tampon sheathing, it is recommended that the circumferential surface 46 of the tampon 30 is smoothed, which can, if appropriate, be carried out with the application of heat. Such a sheathing improves the comfort of introduction and prevents fibers being detached during introduction or removal of the tampon 30 into or from the body cavity. Finally, the tampon 30 can be more weakly radially pressed in the area of its recovery end 34, so that the fibrous material there is less strongly compressed and the expansion of the fibrous material at the recovery end 34 before introduction of the tampon 30 is made easier.

According to an advantageous embodiment of the invention, the circumferential surface of the tampon and its fiber core can be curved in a barrel-shaped manner. As a result of the associated lower compression of the fibrous material over the entire cross section of the tampon in the area of its barrel-shaped convexity, not only the fibrous material in the form of the spiral longitudinal ribs surrounding the solid fiber core, but also the in contrast relatively greatly compressed fibrous material of the fiber core, can, when acted on by body fluid, expand more rapidly and moreover absorb a greater quantity of liquid.

Preferably, the tampons are formed predominantly of fibers. A useful, non-limiting list of fibers includes, cellulosics, polyester, polyvinyl alcohol, polyolefin, polyamine, polyamide, polyacrylonitrile, and the like, and they may have any useful cross-section, including multi-limbed and non-limbed. A useful, non-limiting list of cellulosics includes natural fibers such as cotton, wood pulp, jute, hemp, sphagnum, and the like; and processed materials including cellulose derivatives such as regenerated cellulose (including rayon), cellulose nitrate, carboxymethyl cellulose, and the like. Multi-limbed, regenerated cellulosic fibers have been commercially available for a number of years. These fibers are known to possess increased specific absorbency over non-limbed fibers. Commercial examples of these fibers are Danufil® VY multilimbed viscose rayon fibers available from Acordis Ltd., Spondon, England. These fibers are described in detail in Wilkes et al, U.S. Pat. No. 5,458,835, the disclosure of which is hereby incorporated by reference.

The tampons preferably contain at least a certain quantity of fibers, for example 25%, which are stiffer or more resilient than previously conventional fibers. Such resilient fibers include the Danufil® VY fibers and consequently have a considerably increased memory effect, which increases the absorption capacity of the tampon 30, and polyester fibers.

A preferred apparatus according to the invention for producing the tampon comprises:
  a press having press jaws of equal dimensions which are arranged in a star formation with respect to the press axis x and can be moved synchronously in a common plane radially with respect to the press axis x between their open position and closed position and, in their closed position, are supported on one another on their mutually opposite longitudinal sides;
  a stepped pressing surface on each press jaw,
  the pressing surfaces of the press jaws forming a press opening of round cross section with a length in the range from 40 to 70 mm;
  each pressing surface having a pressing blade which is oriented toward the press opening, and a pressing shoulder, which is arranged only on a specific side flank of the pressing blade and in each case is oriented in the same circumferential direction about the press axis x, the pressing shoulder being offset to the outside in relation to the press axis x with respect to a pressing edge at the free, inner end of the pressing blade, and the area of the pressing shoulder being greater than the pressing edge of the pressing blade of each press jaw, the pressing surface in each case consisting of the pressing blade and the pressing shoulder on each press jaw being spirally shaped.

Figure 5:
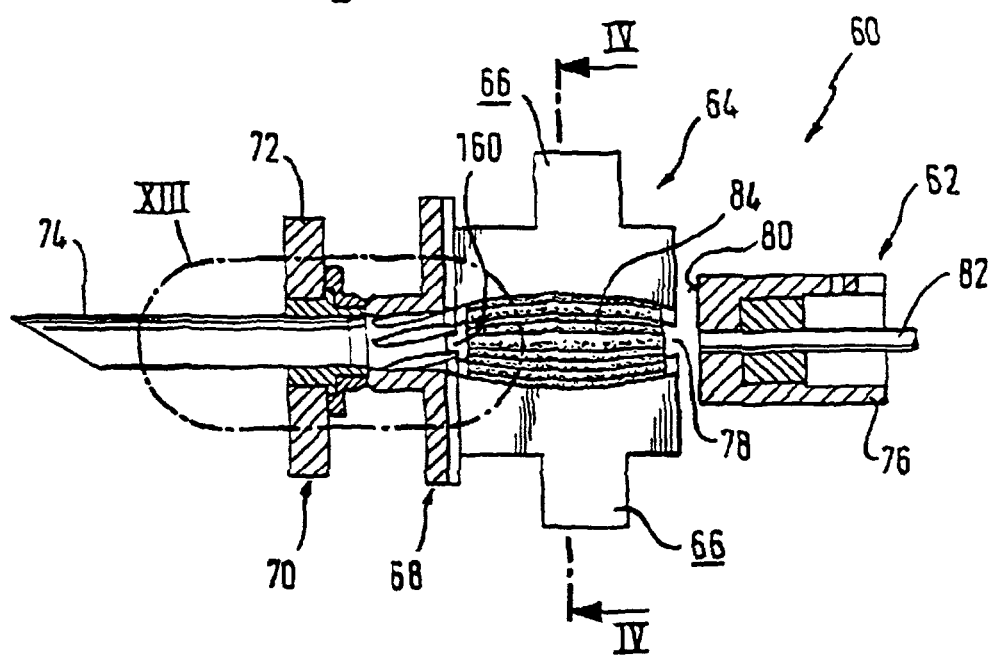
FIG. 5 shows an apparatus for producing tampons according to FIGS. 3 and 4 in a partly sectioned side view.

As FIG. 5 shows, an apparatus 60 for producing the tampon 30 described above consists of a number of elements arranged coaxially one behind another, namely a feed and ejection device 62, a star-shaped press 64 with press jaws 66 which have pressed a preform 84 in their closed or pressing position, a final shaping tool 68 and a circulating or rotating transport apparatus 70. The transport apparatus 70 is, for example, a revolver 72, to which transport sleeves 74 are fixed at equal circumferential angles and radii. The revolver 72 can be moved step by step, so that the transport sleeves 74 can be moved successively in front of the outlet end of the final shaping tool 68 to receive in each case a finished tampon 30 ejected from the final shaping tool 68 by the device 62.

Figure 12:
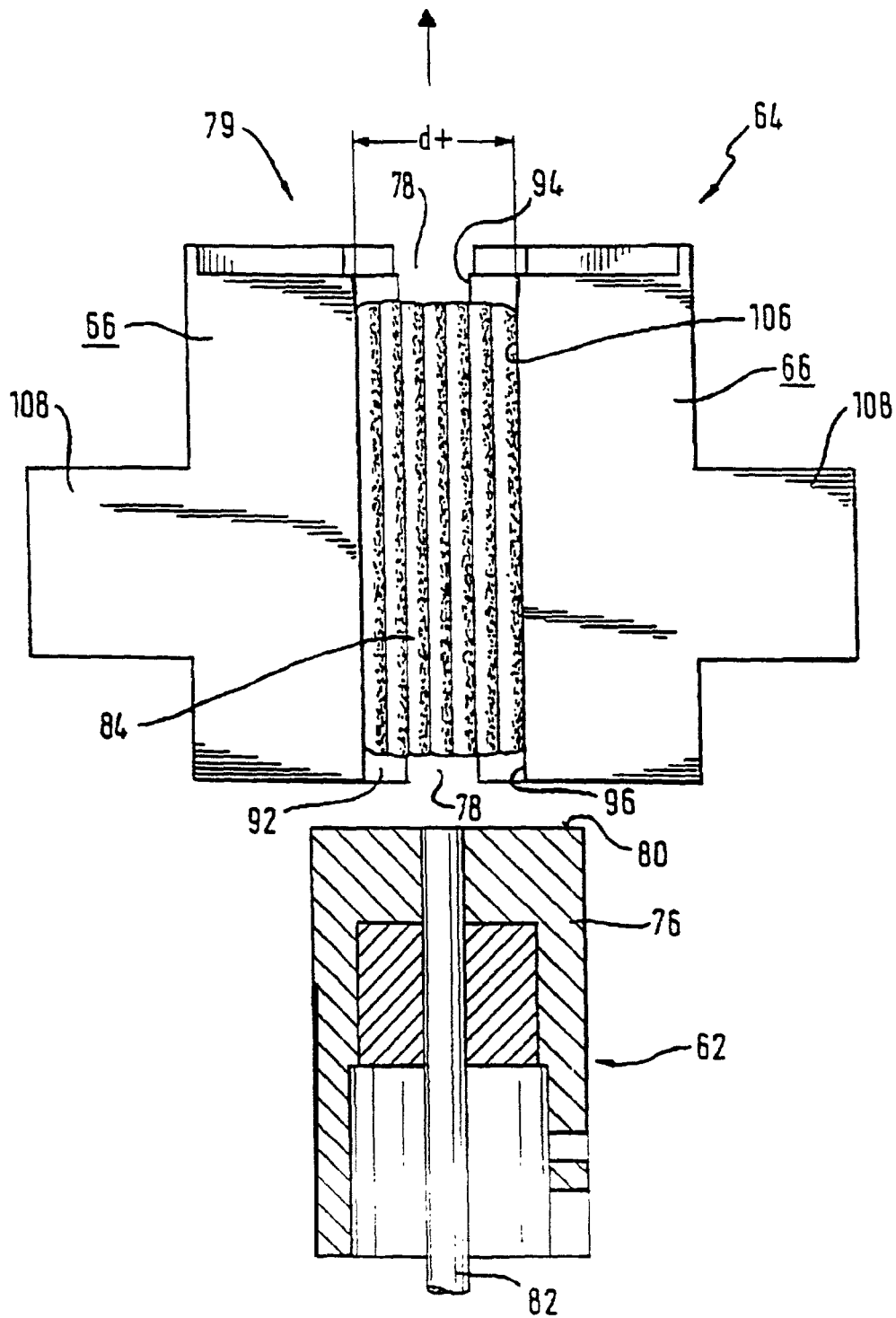
FIG. 12 shows the press in an illustration similar to FIG. 11 but in the clearance dimension, with the preform arranged in it, the circumferential surface of which is substantially cylindrical.

The feed and ejection device 62 according to FIGS. 5 and 12 is known per se and consists of a feed pusher 76 which can be moved to and fro coaxially with respect to a press opening 78 of the press 64. The feed pusher 76 has a circular face 80 with a diameter which corresponds approximately to that of a tampon blank 55 (FIG. 7), preferably of a wound blank, by means of which face the tampon blank 55 can be transferred coaxially into the opened press 64. A bar-shaped ejector 82 is mounted displaceably to and fro relative to the feed pusher 76 coaxially inside the feed pusher 76, the diameter of which ejector is smaller than the press opening 78 in the raised position of the press jaws 66. The ejector 82 serves for, in a single operation, transferring one preform 84 pressed in the press 64 through the final shaping tool 68 into one of the transport sleeves 74 of the revolver 72. In the final shaping tool 68, the preform 84 then takes on the final shape of the finished pressed tampon 30 described above.

Figure 6:
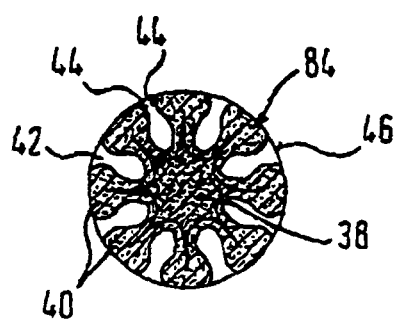
FIG. 6 shows a cross section through a pressed fiber body or preform in a press along the line IV-IV in FIG. 5.

FIG. 6 shows a cross section of the preform 84 in the embodiment of FIG. 5. It can be seen that the cross section of the longitudinal ribs 40 is widened radially outwardly in a drop-shaped manner to the circumferential surface 46 of the preform 84. In contrast, the longitudinal grooves 42 extend radially inwardly in a cross-sectionally drop-shaped manner to the fiber core 38, so that they are wider at the foot of the longitudinal ribs 40 than in the area of the circumferential surface 46 of the preform 84.

Figure 7:
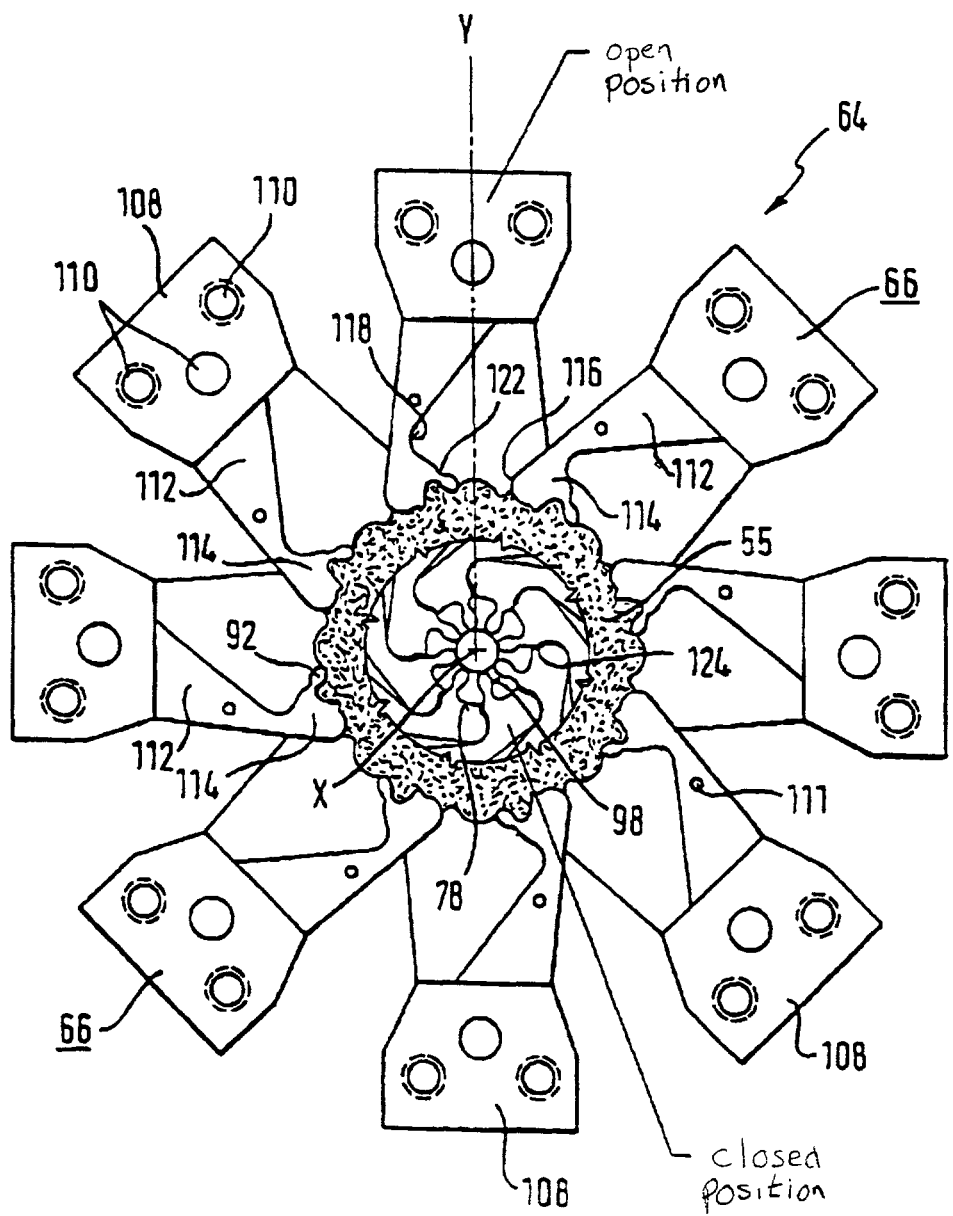
FIG. 7 shows the front side or inlet side of the press, which is shown in the open state with a tampon blank and in the closed state of the press jaws with a preform.
Figure 8:
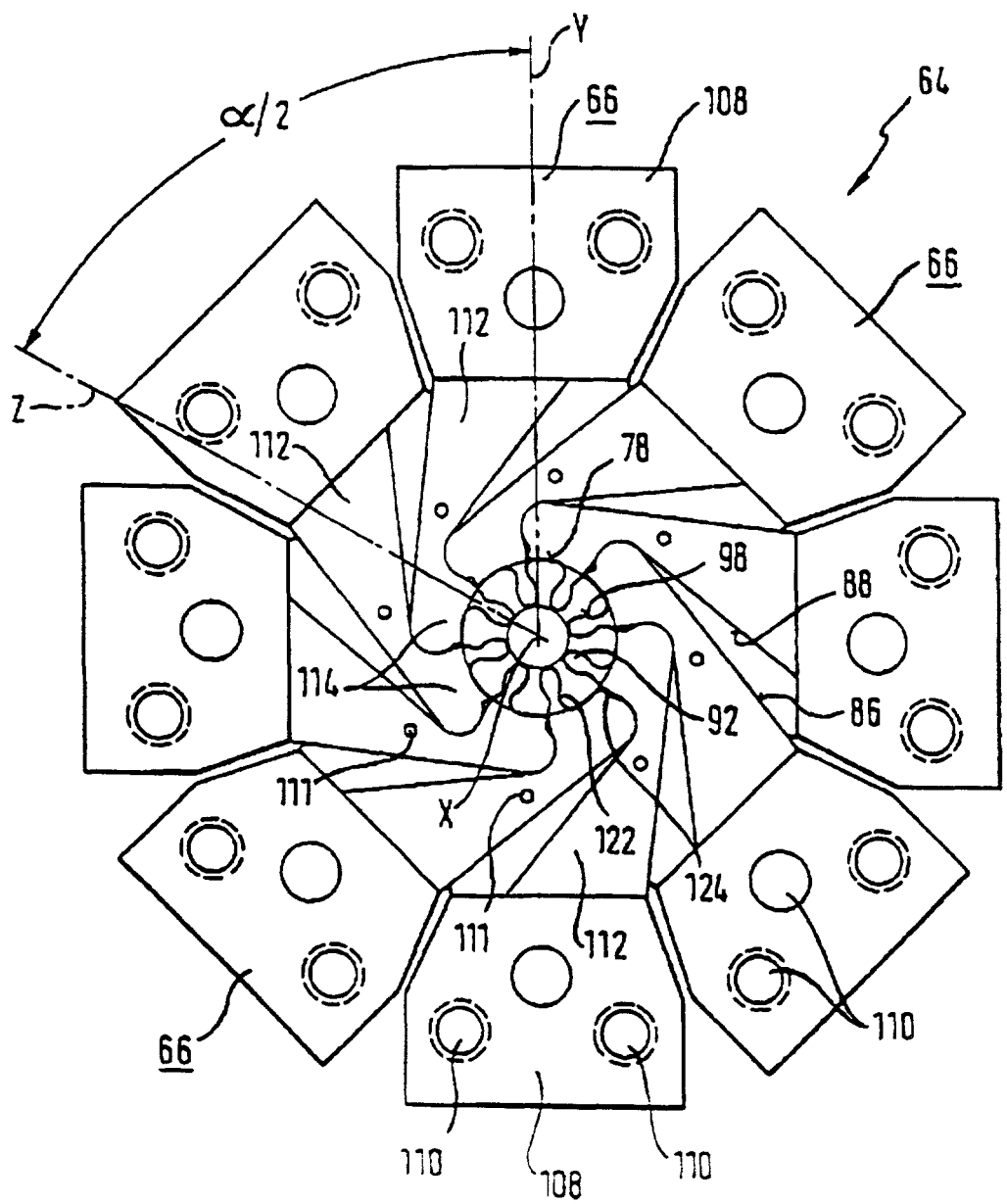
FIG. 8 shows the press according to FIG. 7 in the closed state.

According to FIGS. 7 and 8, a preferred press 64 consists of eight identical press jaws 66 which are arranged in a star formation in a common plane at equal angle intervals about and at the same radial distance from the press axis x. It is desirable to equip the press with an even number of press jaws, but other numbers of press jaws can be used, including odd numbers. The number of press jaws 66 can vary, for example depending on the weight and the composition of the material intended for the tampon 30, and can also be smaller or greater than eight, although the number generally should not be under four. The press jaws 66 have the same dimensions and can be moved to and fro synchronously radially with respect to the press axis x between their open position and closed position (see FIG. 7). In the closed or pressing position, the press jaws 66 are in each case supported on one another on their mutually opposite side walls 86, 88, as is explained in greater detail below.

FIGS. 7 and 8 show the inlet side of the press 64, the press jaws 66 of which are illustrated in the opened and in the closed position in FIG. 7. Each press jaw 66 has a jaw foot 108 with three through-holes 110 for fixing elements (not illustrated) on guide strips (not illustrated).

The profile of the press jaws 66, which can be seen in the front view of the press 64 in FIGS. 7 and 8, extends essentially on that side of a longitudinal mid-axis y of each press jaw 66 which is oriented counterclockwise, in an L-shaped manner from the jaw foot 108 to the press opening 78. The profile of each long L-leg 112 is tapered radially in a triangle-like manner toward a short L-leg 114 and, after this taper, merges at its radially inner end into a striking head 116 (FIG. 7) which has a rounded profile and is a component of the strengthened short L-leg 114 which is angled in the clockwise direction as compared with the long L-leg 112. This angling is in the form of a striking recess 118, the round cross-sectional profile of which extends over an arc of approximately 90° in the direction of the press opening 78 and corresponds to the cross-sectional profile of the striking head 116 of the press jaw 66 adjacent in the clockwise direction. The end of the short L-leg 114 lies at a small distance from the press jaw axis y and forms a pressing blade 92.

A longitudinal mid-axis z of the profile of the pressing blade 92 forms with the longitudinal mid-axis y of the associated press jaw 66 an angle α/2 which in each case opens counterclockwise in relation to the longitudinal mid-axis y of the press jaw 66. This angle α/2 between the longitudinal mid-axis z of the pressing blade 92 and the longitudinal mid-axis y of the press jaw 66 in FIGS. 7 and 8 corresponds to half the circumferential angle α/2, that is to say 60° in the present case, with which each longitudinal groove 42 extends spirally over the circumferential angle of 120° about the press axis x. It follows from this that the profile of the other, rear end (not visible in FIGS. 7 and 8) of the same press jaw 66 is curved in the clockwise direction as compared with the front press jaw profile visible in FIGS. 7 and 8, or encloses an angle with the longitudinal mid-axis y of the press jaw 66 concerned which opens in the clockwise direction in FIGS. 7 and 8 and corresponds to the second half circumferential angle α/2 of 60° of the overall circumferential angle α of 120°.

In the long L-legs 112 of the press jaws 66, a blind hole 111 is in each case arranged in the vicinity of the pressing blade 92 for receiving a heating element. The blind holes 111 are positioned in the best possible manner in order to bring about optimum heating of each press jaw 66. The temperature of the press jaws 66 is in the range from 80° C. to 120° C. and is regulated by means of electronic pulses while observing as small as possible a tolerance range. Each press jaw 66 has its own temperature sensor. The thermal insulation of each press jaw 66 consists of a synthetic material made by the company Ensinger GmbH, 71154 Nufringen, Germany, which is resistant to high temperature and high pressure or compressive force. By heating the press jaws 66, it is possible to reduce the memory effect of modern, highly absorbent, greatly expanding fibrous materials, which occurs after the tampon 30 has been finished. By means of the heated press jaws 66, the surface of the tampon 30 is simultaneously smoothed during pressing and pushing out, and a qualitatively improved surface is produced even in tampons of low weight, the stability of the tampon 30 being preserved. The memory effect of the fibrous material becomes effective again when the fibrous material of the tampon 30 is wetted with body fluid.

Figure 9:
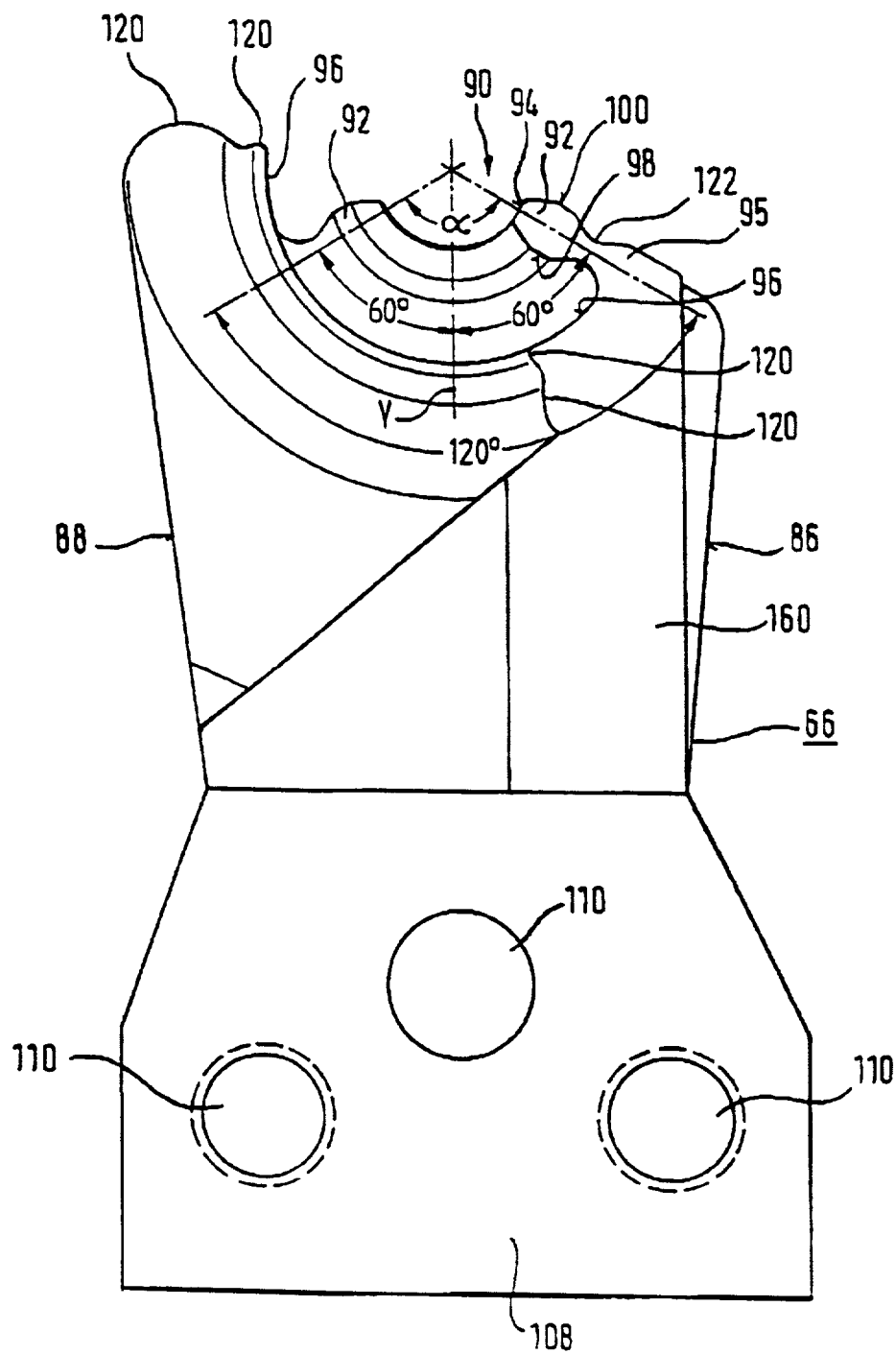
FIG. 9 shows a press jaw in a rear view.
Figure 10:
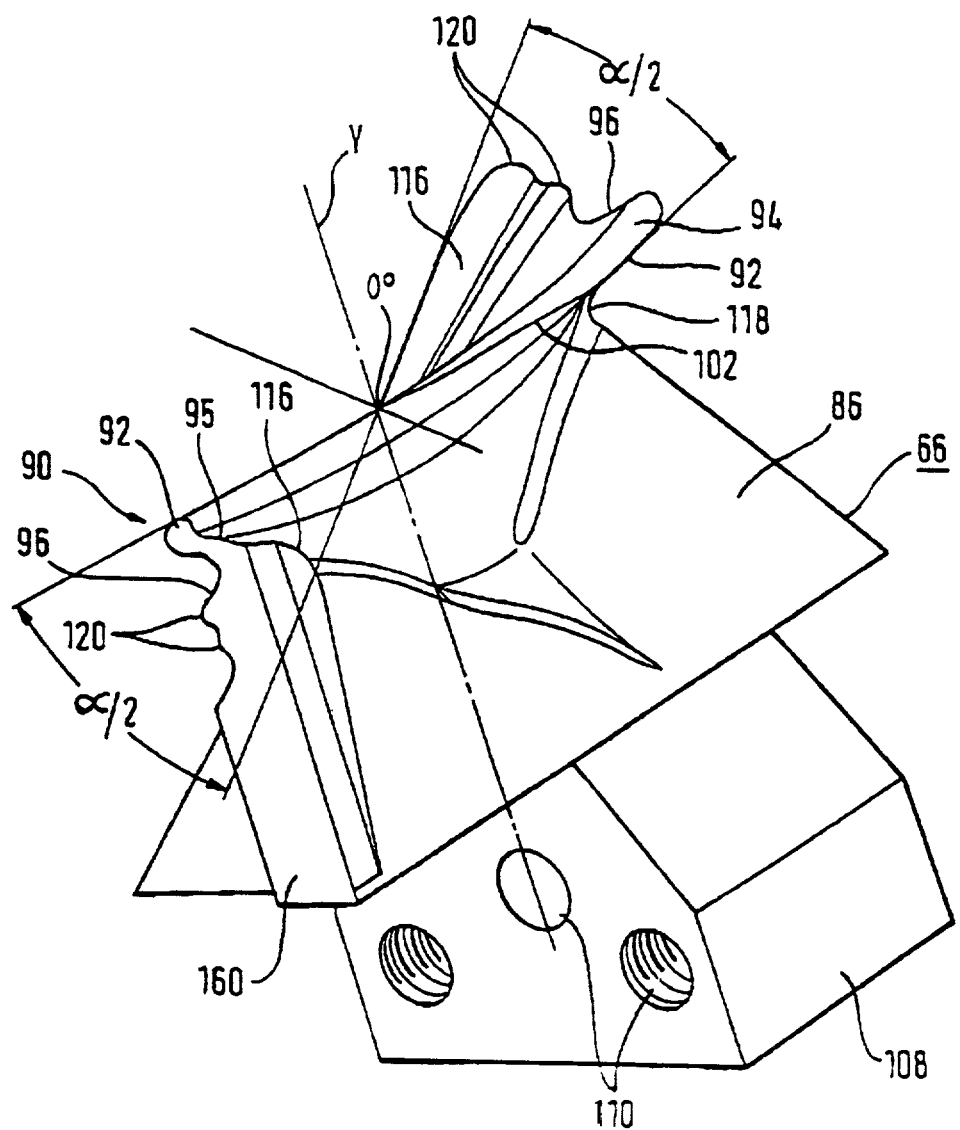
FIG. 10 shows a perspective rear and side view of the press jaw in FIG. 9.

FIGS. 9 and 10 show more clearly that each press jaw 66 has an effective pressing surface 90 which is stepped. These pressing surfaces 90 form a press opening 78 of round cross section with a length in the range from 40 mm to 70 mm. Each pressing surface 90 has a pressing blade 92 which is oriented toward the press opening 78, and a pressing shoulder 96 which is arranged only on a specific side flank 44 of the pressing blade 92, that is to say is in each case oriented in the same circumferential direction about the press axis x. The stepping is brought about by virtue of the pressing shoulder 96 being offset to the outside in relation to the press axis x with respect to a pressing edge 94 at the free, inner end of the pressing blade 92. Furthermore, the area of the pressing shoulder 96 is greater than that of the pressing edge 94 of the pressing blade 92 of each press jaw 66. At the same time, the pressing surface 90 consisting of the pressing blade 92 and the pressing shoulder 96 on each press jaw 66 is spirally shaped. The pressing blade 92 and the associated pressing shoulder 96 of each press jaw 66 can extend over a circumferential angle α of up to at least 150° in the closed or pressing position of the press 64, with a diameter of the press opening 78 in the range from 8 to 17 mm. For the press jaws 66 of the present illustrative embodiment, which are formed in one part, a circumferential angle α of the pressing blade 92 and of the pressing shoulder 96 of each press jaw 66 of 80° to 150°, 120° in the present case, is preferred.

Figure 11:
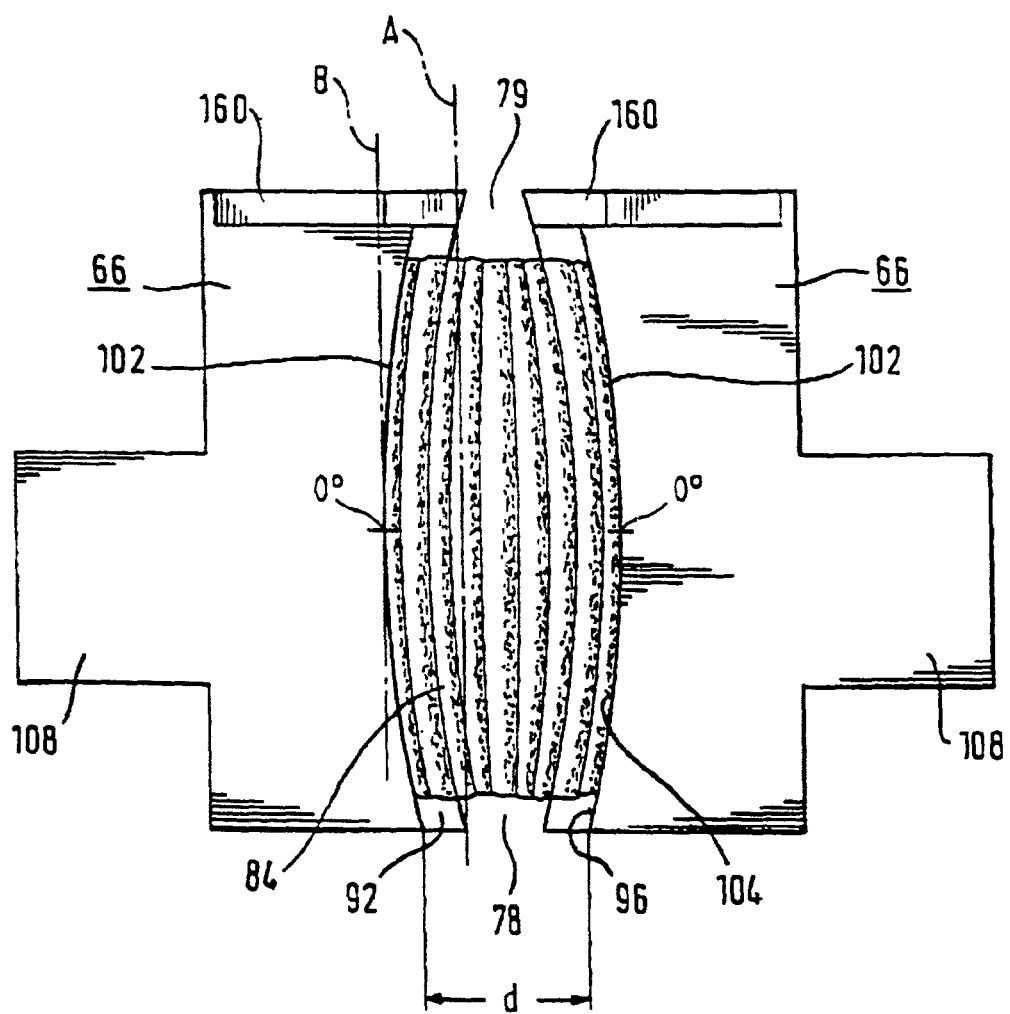
FIG. 11 shows the press in the pressing dimension with a preform arranged in it, the circumferential surface of which is curved in a barrel-shaped manner, in a central longitudinal section.

According to a preferred feature of the present invention, the press jaws 66, when in a pressing position d in FIG. 11, touch an imaginary barrel-shaped envelope surface 104 with their substantially spiral pressing surface 90. In the pressing position, the pressing blade 92 of each press jaw 66 is oriented essentially although not exactly radially with respect to the press axis x (FIGS. 7 and 8). The spiral pressing blades 92 and spiral pressing shoulders 96 of all the press jaws 66, when in a clearance position d+ in FIG. 12, each touch an imaginary, substantially circularly cylindrical envelope surface 106. In this connection, the diameter of the cylindrical envelope surface 106 of the clearance dimension d+ of the press jaws 66 corresponds at least to the greatest diameter of the barrel-shaped envelope surface 104 of the pressing dimension d of the press jaws 66. As a result, improved ejection of the preform from the press is achieved, the high surface quality of the pressed fiber body thus being preserved.

Moreover, the 0° vertex of the arcuate curvature 102 of the spiral pressing surface 90 lies on the longitudinal mid-axis y of each press jaw 66. The pressing surface 90 extends toward its two ends in complementary fashion in each case over half a circumferential angle α/2 in the range of up to at least 75° of the spiral pressing surface 90 of the press jaw 66. This situation is explained in greater detail below.

The cross section of the pressing blade 92 is drop-shaped, the greatest thickening lying behind the front, narrow, rounded pressing edge 94, and a neck-like contraction 122 being present toward a pressing blade foot 95. The pressing shoulder 96 is arranged eccentrically with respect to the pressing blade 92, in each case only on one specific side surface of two side surfaces 98, 100 of the pressing blade 92 (FIG. 9). This specific side surface 98 or 100 of all the press jaws 66, which adjoins the pressing shoulder 96, is in each case uniformly oriented only in the clockwise direction or counterclockwise. In FIGS. 7 and 8, which show the front side of the press 64, this side surface 98 of the pressing blade 92 facing toward the pressing shoulder 96 is in each case oriented counterclockwise. In this connection, each pressing shoulder 96 is offset to the outside radially in relation to the press axis x with respect to the narrow pressing edge 94 of the pressing blade 92 by the radial distance between the fiber core 38 and the circumferential surface 46 of the preform 84, and has in the circumferential direction of the press opening 78 a greater area than the pressing edge 94 of the pressing blade 92. The center of curvature of the pressing shoulders 96 of all the press jaws 66 then lies on the axis x of the press 64 only in the clearance position d+ of the press jaws 66.

According to FIGS. 9 and 10, which show the end face of a press jaw 66 at the rear or outlet side of the press 64, the pressing shoulder 96 is, in contrast, oriented in the clockwise direction. The pressing surface 90, consisting of the pressing blade 92 and the pressing shoulder 96, of each press jaw 66 runs spirally with respect to the press axis x of the press opening 78. In this connection, the pressing blade 92 and the associated pressing shoulder 96 of each press jaw 66 extend over a circumferential angle of 120° of the pressed preform 84 between the two ends of the same. Half the circumferential angle α/2 extends in each case over 60° in the present case in a symmetrical or complementary fashion on both sides of the longitudinal mid-axis y of each press jaw 66, so that the press jaw 66 is loaded uniformly over its entire cross section by the pressing forces exerted.

The pressing blades 92 and pressing shoulders 96 of each press jaw 66 are not only curved spirally in the longitudinal direction corresponding to the described circumferential angle α of the tampon 30 of 120°, but also have a curvature 102 (FIGS. 10 and 11) from one end of the press jaw 66 to the other end of the same press jaw 66. This curvature 102 ensues from the fact that the effective pressing surface 90 of each press jaw 66 has to press a spiral longitudinal groove 42 which must in each case extend over a specific circumferential angle of the preform 84, that is to say in the present case over 120° of the circumferential surface of the approximately cylindrical tampon blank 55 at a specific angle of inclination β (FIG. 3). In this connection, the tampon blank 55 (FIG. 7) is as a whole compressed to the pressing dimension d of the preform 84 (FIG. 11), at which each pressing blade 92 is moved beyond the position which is radial with respect to the press axis x. As a result, the clear cross section of the press opening 78 formed by the press jaws 66 widens from both its ends to the longitudinal center of the press jaws 66 or of the press opening 78 formed by these, which consequently assumes a barrel shape in the pressing dimension d or in its pressing position. The envelope surface 104 touching the pressing blades 92 or the pressing shoulders 96 therefore has a slightly barrel-like contour (see FIGS. 5 and 11) which therefore narrows toward both ends of the press opening 78. Accordingly, the preform 84 also assumes a corresponding shape in the press 64, as can be seen from FIGS. 5 and 11. In order that the preform 84 can be ejected perfectly, that is to say without damage to the fibrous structure on its surface, from the press 64 while being rotated about its longitudinal axis, the press jaws 66 have to be raised by a specific dimension d+ (FIG. 12). This clearance dimension d+ corresponds at least to the radial distance which separates a chord A, which interconnects the two ends of the pressing blade 92 of a press jaw 66 in FIG. 11 and runs parallel to the press opening 78, from a tangent B in FIG. 11, which is placed against a vertex 0° of the radially outwardly arcuate curvature 102 of a pressing blade 92 and is likewise oriented parallel to the press opening 78. In addition, the clearance dimension d+ can be defined in such a way that it must correspond at least to the greatest diameter of the barrel-shaped envelope surface 104, which is touched by the pressing blades 92 or pressing shoulders 96 in the pressing position. In the case of a tampon 30 with a diameter of 13 mm, this clearance dimension=d+0.6 mm, by which the press jaws 66 must be moved radially outwardly in order to form, according to FIG. 12, the circularly cylindrical envelope surface 106 of the press opening 78. In this connection, the pressing blades 92 or pressing shoulders 96 touch the circularly cylindrical envelope surface 106 spirally over essentially the entire length in the clearance dimension d+ and consequently form a circularly cylindrical press opening 78 for the ejection of the preform 84.

FIGS. 7 and 8 show clearly that the neck-shaped contraction 122 of each pressing blade 92 brought about by the drop shape makes possible a greater displacement of the fibrous material approximately radially outwardly during pressing. As a result, the pressing dimension of the press jaws 66 can be reduced to, for example, 4 mm from previously 4.8 mm of the diameter of the fiber core 38 with the same stability and improved absorption capacity and with the soft surface of the tampon 30 being preserved. Furthermore, the width of the rounded pressing edge 94 can be reduced, in order to make it possible for the fibrous material to flow into the radially outwardly created free space of the press opening 78. In this way, the quantity of fiber necessary for producing the fiber core 38 can be reduced in favor of that quantity of fiber which, with the same stability of the tampon, is available for immediate liquid absorption after introduction of the tampon into the body cavity.

In order to be capable of receiving the outwardly displaced fibrous material, the pressing shoulder 96 has a reduced shoulder radius of 6.2 mm in the present illustrative embodiment, compared with 6.55 mm previously, and extends in profile approximately parallel to that side of the press jaw 66 oriented counterclockwise, which merges into the short L-leg 114 and forms the striking head 116.

The outward displacement of the fibrous material achieved by means of this shape of the press jaws 66 makes possible a saving of fibrous material which, in the illustrative embodiment described of a digital tampon 30 with a final diameter of 13 mm and a length of 50 mm.

It can be seen in particular from FIGS. 9 and 10 that at least one squeezing rib 120 is provided on an outer side of the pressing shoulder 96 approximately at the level of the latter. In the closed state (pressing dimension d) of the press 64, this squeezing rib 120 of the pressing shoulder 96 and also the striking head 116 of each press jaw 66 bear against the rounded striking recess 118 of the adjacent press jaw 66 in front of the neck-shaped contraction 122 of the pressing blade 92 (FIGS. 7 and 8). The outer side of each pressing shoulder 96 is provided in FIGS. 9 and 10 with two parallel squeezing ribs 120 which close a gap 124 oriented approximately radially with respect to the press axis x between the striking head 116 and the striking recess 118 of adjacent press jaws 66 in relation to the press opening 78 and thus in each case in relation to the radially outer side of a spiral longitudinal rib 40 of the preform 84. As a result, the penetration of fibrous material of the tampon blank 55 into the gap 124 between adjacent press jaws 66 is essentially precluded. In the event that fibers penetrate the gap 124 between adjacent press jaws 66, the squeezing ribs 120 cut the staple length of these fibers, so that the fiber residues can fall out of the press 64 and be extracted by suction. A burr-free, smooth, soft, radially outer surface of each spiral longitudinal rib 40 is consequently formed.

FIGS. 9 and 10 show clearly that at one end face the striking head 116 protrudes further radially inwardly than the pressing blade 92 which is set back by the width of the pressing shoulder 96 with respect to the striking head 116 and is angled in relation to the latter toward the side facing away from the striking head 116. By means of the side walls 86, 88, the press jaws 66 have a cross section normal to their longitudinal mid-axis y which has a shape which is complementary to the circumferential angle α of the spiral press jaw curvature 102, so that the abovementioned uniform distribution of the pressing forces exerted in each case by the press jaws 66 over their entire cross section, that is to say in the direction of the longitudinal mid-axis y of the press jaws 66, is guaranteed.

FIG. 11 illustrates the pressing dimension d of the press 64 diagrammatically. This pressing dimension d corresponds to the barrel-shaped envelope surface 104 which is formed by the spiral pressing blades 92 and pressing shoulders 96 of the press jaws 66 of the press 64 in the closed state or pressing dimension d. This pressing dimension d is, depending on the particular composition and purpose of the tampon 30 concerned, between 6 and 17 mm, 13 mm in the present illustrative embodiment, at the inlet end and at the outlet end of the closed press 64.

During ejection of the preform 84 from the press 64 in this pressing position shown in FIG. 11, the ejection forces would increase greatly as a result of the barrel-shaped cross section of the press opening 78 and of the preform 84 situated therein. The fibers on the surface of the preform 84 would be torn out of the fiber composite, the smooth surface of the preform 84 would be correspondingly damaged and a fiber loss would be caused. For this reason, provision is made that, after the opening of the press 64 to the given clearance dimension d+, the imaginary envelope surface 106 formed or touched by the pressing blades 92 or the pressing shoulders 96 is circularly cylindrical, so that the preform 84 can be ejected from the press 64, virtually without any appreciable resistance, through the final shaping tool 68 into the transport sleeve 74 with simultaneous rotation as a result of the spiral pressing blades 92 engaging in the longitudinal grooves 42 of the preform 84.

In FIG. 12, the spiral pressing blades 92 and pressing shoulders 96 of the press jaws 66 have been moved back radially outwardly by a given clearance dimension d+ of, in the present illustrative embodiment, d+0.6 mm in relation to the pressing dimension d shown in FIG. 11, in order to enclose or touch the imaginary circularly cylindrical envelope surface 106, which allows the preform 84, which has been pressed in a barrel shape and provided with spiral longitudinal ribs 40 and spiral longitudinal grooves 42, to be pushed out of the press 64 with substantially reduced friction by means of the ejector 82 in the feed pusher 76.

According to FIG. 12, the pressing blades 92 and the pressing shoulders 96 of all the press jaws 66 therefore each touch the imaginary, circularly cylindrical envelope surface 106 on a spiral line over at least a considerable part of their length. That is to say if a lower degree of compression of the fibrous material is desired at the recovery end 34 of the preform 84, the radial distance of the effective pressing edges 94 from the press axis x in the area of the outlet side 79 of the press opening 78 is dimensioned to be somewhat greater, in the closed state of the press jaws 66, than over the remaining longitudinal area of the pressing edges 94, so that this part of the pressing edges 94 would not touch the circularly cylindrical envelope surface 106 in the clearance dimension d+ of the press jaws 66 but would lie slightly radially outside this circularly cylindrical envelope surface 106.

Figure 13:
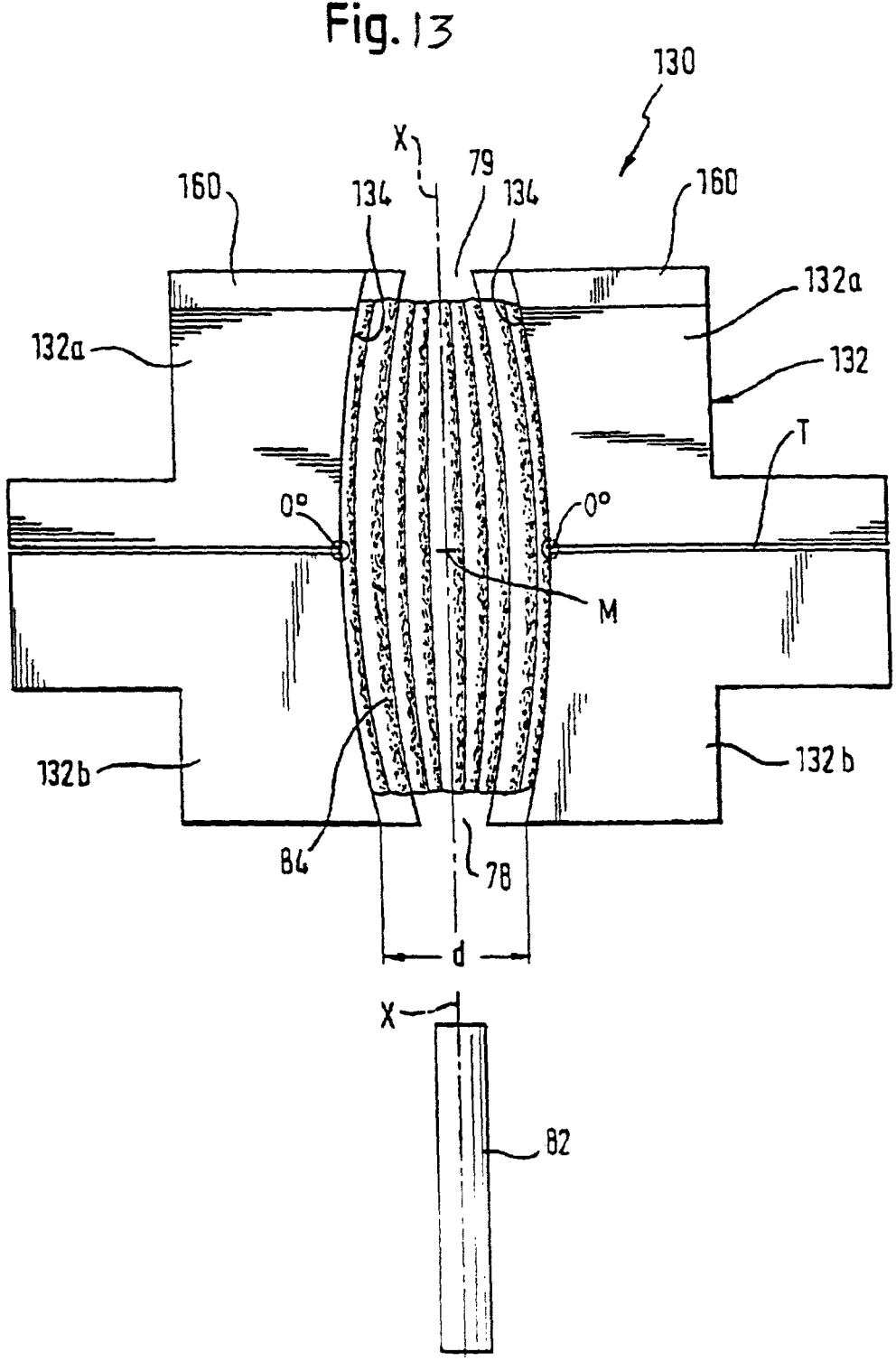
FIG. 13 shows a press with divided press jaws in the pressing dimension in a central longitudinal section.
Figure 14:
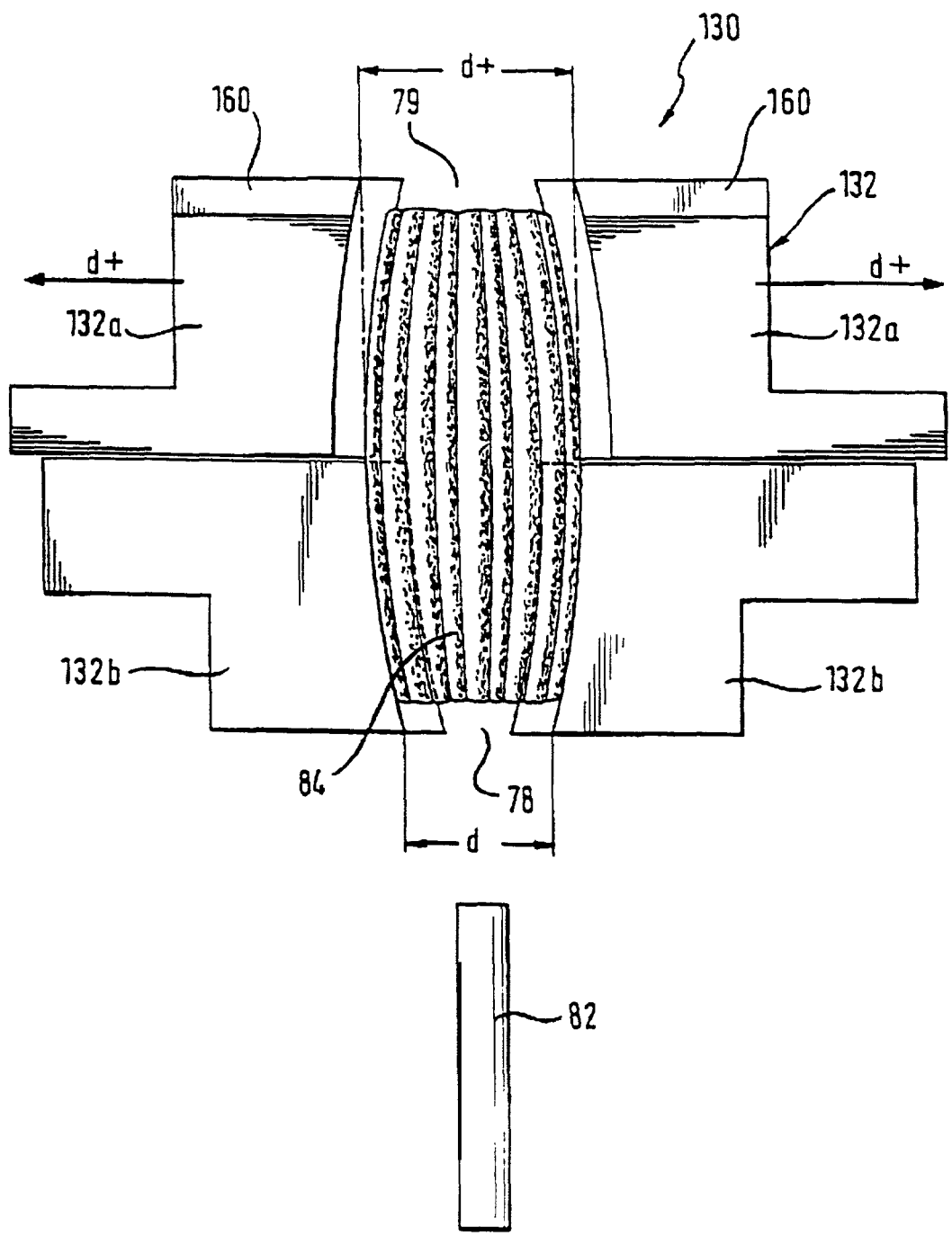
FIG. 14 shows the press in FIG. 13 in the clearance position of the press jaws for ejection of a preform.

FIGS. 13 and 14 show an embodiment of a press 130 with multi-part press jaws 132. The divided press jaws 132 can be moved to and fro radially with respect to the press axis x independently of one another. The press jaws 132 are divided in at least one plane T which is oriented at right angles to the press axis x. In the present illustrative embodiment, the press jaws 132 are of two-part design. The dividing plane T of the two-part press jaws 132a, 132b intersects the 0° vertex of their pressing surface 134 and the axis x of the press 130, at the longitudinal center M of the same. The press-jaw halves 132a associated with the outlet side 79 of the press 130 can be moved radially outward into the clearance position d+ from their pressing position d in relation to the press axis x in order to make possible ejection of the preform 84 from the press (FIG. 14) with greatly reduced friction. By multiple division of the press jaws 132 transversely to the press axis x and depending on the number of press jaws 132, the circumferential angle α can be extended beyond 150°. Furthermore, suitable design of the press jaws also makes it possible to modify the outer contour of the tampon depending on the specific tampon requirements.

From the above description of the press jaws 66; 132 according to the invention, it is preferred that the press jaws lie diametrically opposite one another in pairs. The present invention also includes the possibility of, in addition to the press jaws 66; 132 described, which produce the fiber core 38, building press jaws into the press 64; 130 which serve purposes other than the production of the fiber core 38. Accordingly, it is possible to use press jaws within the press 64; 130 in order, for example, to stamp patterns or depressions onto or into the surface of the tampon 30 during pressing of the preform 84, which are intended to serve decorative and/or physical purposes.

Figure 15:
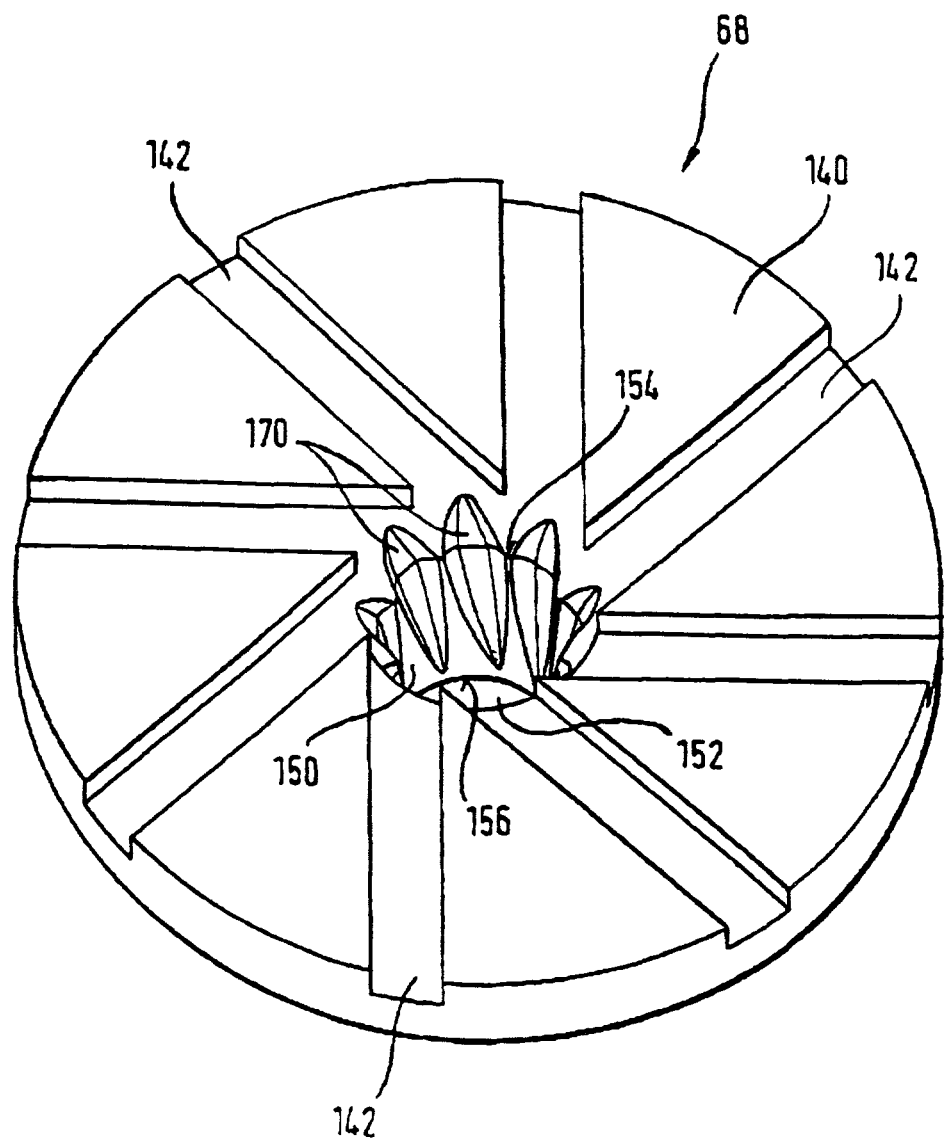
FIG. 15 shows a perspective view of the inlet side of a final shaping tool.
Figure 16:
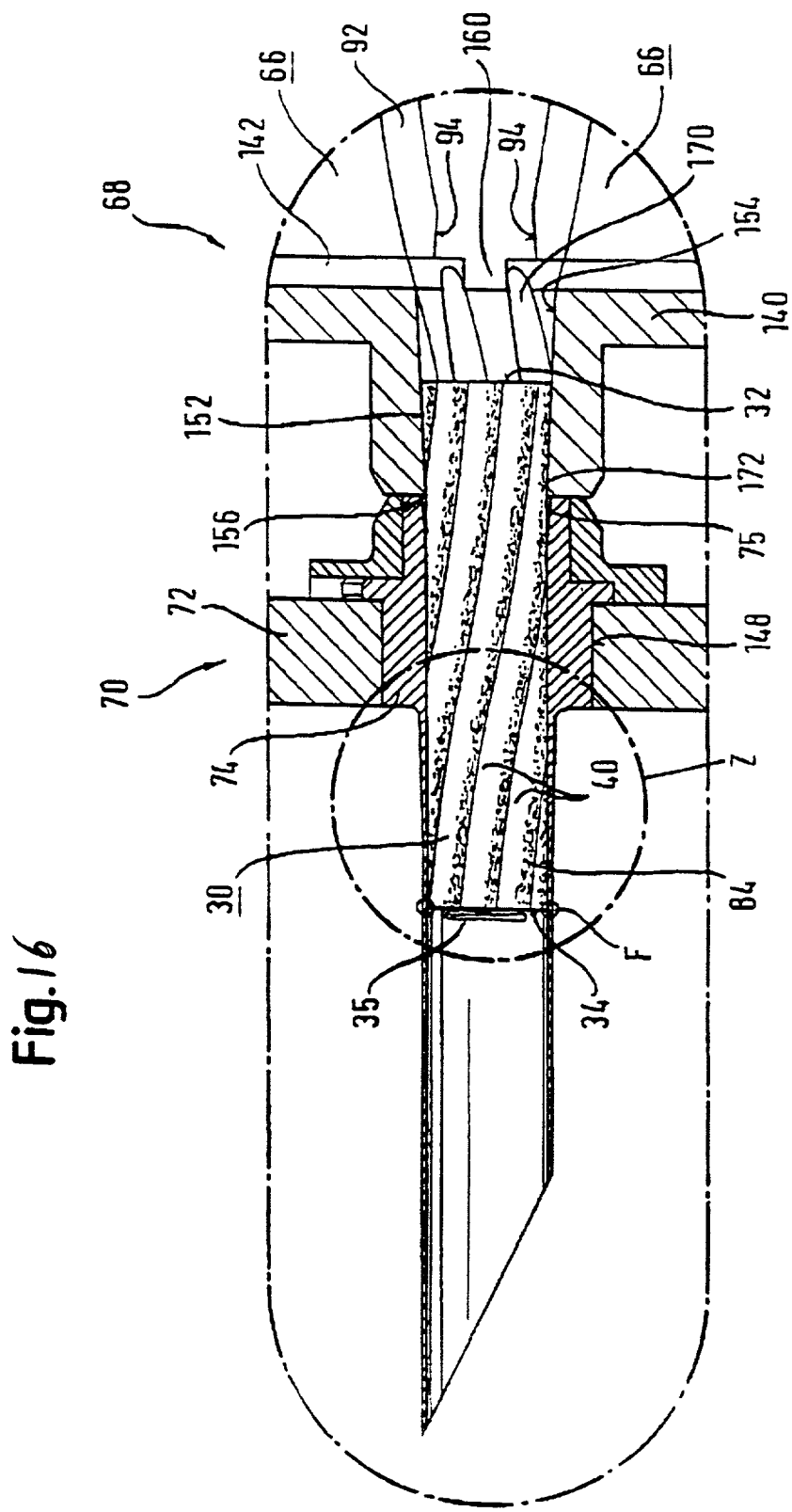
FIG. 16 shows a detail XIII of FIG. 5 on larger scale with a view of a tampon.
Figure 17:
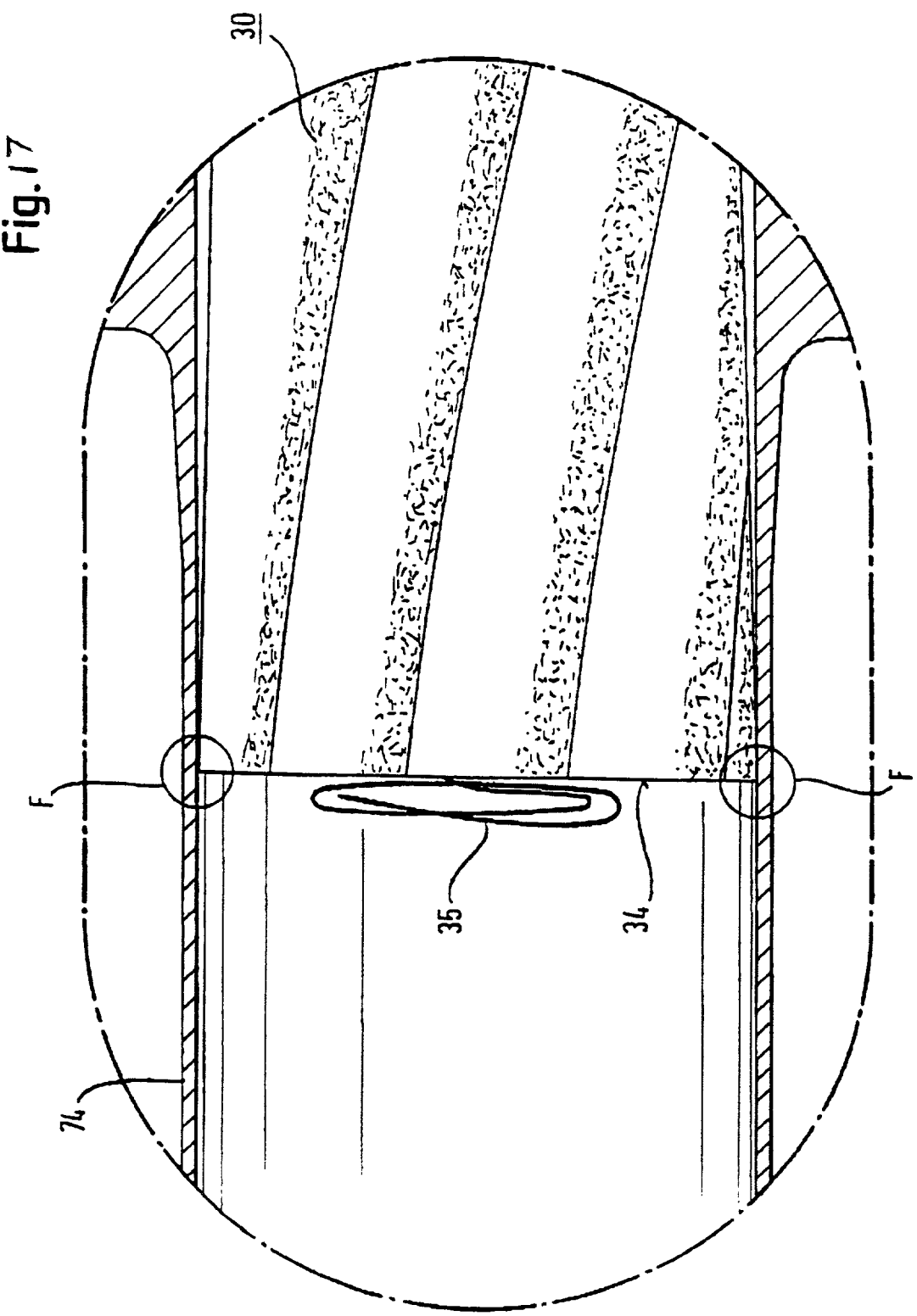
FIG. 17 shows a detail Z of FIG. 16 in a greatly enlarged illustration.

FIGS. 15, 16 and 17 show the final shaping tool 68, which consists of a guide plate 140 which is arranged in a stationary manner immediately behind and coaxially with the press 64 and is designed in one piece with a smoothing bush 150 for the preforms 84. The final shaping tool 68 includes a conical final shaping channel 152 for the preforms 84, which extends through the guide plate 140 and the smoothing bush 150. As shown in FIG. 5, the guide plate 140 is arranged immediately in front of the outlet side 79 of the press 64 and, as already described in U.S. Pat. No. 5,911,712, is provided on its side facing the press 64 with a number of grooves 142 corresponding to the number of press jaws 66; 132, which are arranged at the same circumferential angle intervals as the press jaws 66; 132. According to the invention, the grooves 142 extend at a distance from and parallel to the press jaw axis y in the direction of the press opening 78 tangentially with respect to the final shaping channel 152.

It can be seen from FIGS. 5 and 9 to 14 that the press jaws 66; 132 are each provided at their rear end with a positioning web 160 which projects with respect to the outlet side 79 of the press 64 and in each case engages in one of these grooves 142 with lateral play. The inner, free front end of the positioning webs 160 is a component of the pressing surface 90; 134 of the press jaws 66; 132 and reaches over an axial gap between the press 64; 130 and the final shaping tool 68. In their clearance position d+, the pressing surfaces 90; 134 of the press jaws 66; 132 have a slightly smaller diameter than the inlet opening 154 of the smoothing bush 150. This allows the positioning webs 160 to maintain the centered position of the recovery element 35 (previously wound spirally at the recovery end 34 of the tampon blank 55 lying at the front in the transport direction x (FIGS. 16, 17)) during the pressing and the ejection of the tampon 30 from the press 64. From the circular inlet opening 154, the final shaping channel 152 tapers conically to an outlet opening 156 of the smoothing bush 150. In this connection, the conical shape of the smoothing bush 150 is designed in such a manner that as small as possible an ejection force is necessary in order to push the preform 84 out of the press 64 through the smoothing bush 150 and to compress it concentrically to the final dimension of the tampon 30.

FIGS. 5 and 14 to 16 show that the final shaping tool 68 is provided with spirally shaped, radially inwardly projecting smoothing ribs 170, the number of which corresponds to that of the press jaws 66 and the angle of inclination β of which corresponds to that of the spiral pressing blades 92. The spiral smoothing ribs 170 engage directly in a lightly concentrically pressing and smoothing manner in the spiral longitudinal grooves 42 of the preform 84 leaving the press 64, so that the profile of the preform 84 is preserved but the widening of the cross section of the fiber core 38 caused by the barrel shape of the preform 84 is reduced. The smoothing bush 150 can be heated to a temperature of 80° to 120° C. in order, if desired, to optimize the smoothing effect. The smoothing ribs 170 end at a distance in front of the outlet opening 156 of the smoothing bush 150 and merge into a smooth cylindrical end section 172 of the smoothing bush 150. This end section 172 of the smoothing bush 150 has a diameter which corresponds to the diameter of the finished pressed tampon 30. In this smooth cylindrical end section 172 of the smoothing bush 150, the spiral longitudinal grooves 42 of the preform 84, which were open up to here, are closed at the radially outer ends of the side flanks 44 of adjacent spiral longitudinal ribs 40 to the final diameter of the tampon 30 (FIG. 4). In this way, the longitudinal grooves 42 become the liquid guide ducts 50 which are preferably open toward both ends of the tampon 30 (FIGS. 3 and 4).

In FIGS. 5, 14 and 15, the transport apparatus 70 is illustrated in an essentially cut-away manner and consists in the present case, as part of a circulating or rotating transport system, of a revolver 72. The revolver 72 is provided with a transverse hole 148, in which the cylindrical transport sleeve 74 fits and is fixed at right angles to the circulating plane of the revolver 72. The transport sleeves 74 are fixed to the revolver 72 at equal circumferential angle intervals and radii, so that in each case one transport sleeve 74 can be moved successively step by step in front of the outlet opening 156 of the smoothing bush 150, in order to feed a finished pressed tampon 30 to a further production station. In this production station (not shown), as is known per se, the insertion end 32 can be provided with the round dome 52 at the same time as the recovery end 34 is provided with the finger recess 48.

As the tampon 30 is subjected to rotation by the spiral press jaws 66 and the spiral smoothing ribs 170 in one single operation on ejection from the press 64 through the smoothing bush 150 into the transport sleeve 74, the cylindrical transport sleeve 74, which is widened conically over a short length at its inlet opening, ensures that the high quality of the surface and of the fibrous structure of the tampon 30 is preserved. In this connection, this delayed laying of the tampon 30 against the cylindrical inner wall of the transport sleeve 74 is caused by the expansion of the fibrous material of the finished pressed tampon 30, that is to say that the diameter of the transport sleeve 74 is dimensioned to be correspondingly greater so as to allow for this expansion of the fibrous material of the tampon 30 immediately after pressing. This is because a positive contact of the tampon 30 against the cylindrical smooth inner wall of the transport sleeve 74 takes place only, as a result of its expansion after pressing, when the tampon 30 concerned has, with its recovery end 34 lying at the front, almost or completely left the outlet opening 156 of the smoothing bush 150.

Furthermore, it can be seen in FIG. 16 that the outlet-side spiral pressing edges 94 of the press jaws 66, which edges lie opposite one another in pairs, form an angle which widens to the outlet end 79 of the press 64. As a result, the fiber core 38 is more weakly pressed at the recovery end 34 of the preform 84, so that the fibrous material can be spread slightly before use so as to facilitate digital introduction of the tampon.

In FIG. 17, the incipient expansion of the tampon 30 and its resulting contact against the cylindrical inner wall of the transport sleeve 74 at F is shown especially clearly owing to the enlarged illustration. The fact that the tampon 30 expands only once it is in the transport sleeve 74 on account of the memory effect of the greatly expanding fiber proportion, can be attributed to the high production speed of the tampon. Associated with this is the considerable advantage that the rotary movement to which the tampon 30 is subjected during ejection encounters no appreciable resistance, so that the spiral fibrous structure of the tampon achieved by the invention is preserved in its full extent.

The method of producing the tampon according to a preferred embodiment of the invention comprises the steps:
  providing a tampon blank of tangled fibrous material;
  compressing the tampon blank on narrow generating lines of its circumferential surface, which are separated from one another by equal circumferential angles, forming longitudinal grooves and a substantially cylindrical fiber core with a high degree of compression, from which relatively uncompressed longitudinal ribs extend radially outward, the tampon blank being pressed on spiral generating lines in order to form spiral longitudinal grooves and spiral longitudinal ribs parallel thereto in order to enlarge the absorbent surface of the tampon.

In detail, the preferably cylindrical tampon blank 55, the recovery end 34 of which lies at the front in the feed direction or in the direction of the press axis x, is then introduced coaxially into the press 64 by means of the feed pusher 76. Subsequently, the tampon blank 55 is radially compressed by the press jaws 64 in each case over identical, narrow, spirally shaped sections of identical angle of inclination β of its circumferential surface, which sections are separated from one another by equal circumferential angles. In this way, a preform 84 of preferably barrel-shaped contour is produced, with spirally running longitudinal grooves 42 on a solid fiber core 38 with a high degree of compression which is substantially cylindrical but, because of the barrel shape, is widened in cross section at mid-length, and with longitudinal ribs 40 which extend radially outwardly from the fiber core 38 and run spirally in the longitudinal direction of the preform 84. In this connection, the spirally shaped sections are in each case pressed over a circumferential angle α of up to at least 150°, preferably over an angle of 80° to 120°, in the present case over an angle of 120°. In the press 64, the fibrous material is preferably subjected to lower radial compressing pressure in the area of the recovery end 34 of the tampon blank 55 than the remaining fibrous material of the tampon blank 55. The tampon blank 55 is, depending on the properties of the fibrous material used, in particular in the event of use being made of highly expansive fibers of irregular cross section with a strong memory effect, pressed at a temperature of the press jaws 66 of 80° to 120° C. to the final shape of the tampon 30, in order to achieve the desired dimensional stability of the fibrous material by eliminating the memory effect of the fibers, which immediately becomes effective again on contact with bodily fluid and thus increases the expansion and absorption speed of the tampon 30 with the least possible use of fibrous material.

In the press 64; 130, the tampon blank 55 is compressed in a single pressing operation to form the barrel-shaped preform 84 which, on ejection from the press 64, may be at the same time subjected to final shaping in the downstream, if appropriate heatable, smoothing bush 150. This final shaping includes a weak radial pressure being exerted on the outer ends of the spiral longitudinal ribs 40 and on the spiral longitudinal grooves 42 by the smoothing bush 150, which can be heated to 80° C. to 120° C. if so desired, and its smoothing ribs 170. This weak radial pressure has the effect that the outer ends of the mutually opposite side flanks 44 of adjacent longitudinal ribs 40 are pressed against one another by the smooth, circular cross section of the final shaping channel 152 in the area of the outlet opening 156 of the smoothing bush 150, so that the longitudinal grooves 42 and thus the outer, approximately cylindrical, soft, closed circumferential surface 46 of the tampon 30 are shaped, and the spiral liquid guide ducts 50 are produced in the area of the now radially outwardly closed longitudinal grooves 42, which ducts are preferably open at the insertion end and at the recovery end of the tampon. In this way, a considerable increase in the absorption capacity of the tampon is achieved along with very comfortable introduction for the user. Furthermore, the smoothing ribs 170 may reduce slightly the cross-sectional widening of the fiber core 38 caused by the barrel shape of the preform 84 of this embodiment.

On the exit, associated with the rotary movement, of the finished pressed tampon 30 from the smoothing bush 150 into the transport sleeve 74 of the transport apparatus 70, the newly compressed fibrous material expands in relation to the very smooth, cylindrical inner wall of the transport sleeve 74, without frictional resistance, which would impair the surface quality, occurring between the cylindrical, smooth inner wall of the transport sleeve 74 and the fibrous material on the surface of the tampon 30, so that the high quality of this tampon 30 provided with spiral longitudinal ribs 40 and longitudinal grooves 42 is ensured even in the case of mass production. In this connection, it is important that the direction of rotation, in which the length of a fibrous nonwoven, at the end of which a sheathing material is fixed on the outside, is wound up to form a tampon blank 55, is also maintained by the spiral press jaws and smoothing ribs, in order that the embedding of the free, outer end of the sheathing material strip in the surface of the tampon 30 is maintained.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A tampon comprising compressed fibrous material and a flexible recovery element, the tampon is dimensionally stable, is arranged and configured for digital insertion, and has an insertion end, a recovery end, a longitudinal axis, and a substantially cylindrical outer surface, wherein said outer surface of the tampon is at least partially provided with spirally shaped, longitudinal grooves, wherein the tampon has sufficient column strength to permit digital insertion thereof into a body cavity.

2. The tampon according to claim 1 wherein the tampon expands substantially radially with respect to the longitudinal axis upon absorption of bodily fluid.

3. The tampon according to claim 1 wherein the tampon comprises a tampon core having a first density from which core fibrous longitudinal ribs extend radially outward that are defined by said spirally shaped, longitudinal grooves.

4. The tampon according to claim 3 wherein said longitudinal ribs comprise fibrous material having a second density less than the first density.

5. The tampon according to claim 3 wherein said longitudinal ribs extend radially outward at equal circumferential angle intervals and between the insertion end and the recovery end.

6. The tampon as claimed in claim 3, wherein a circumferential surface of the fiber core is substantially cylindrical.

7. The tampon as claimed in claim 1, wherein the spiral longitudinal grooves each extend over a circumferential angle of up to at least 150° of the tampon.

8. The tampon as claimed in claim 7, wherein the circumferential angle is about 80° to about 120°.

9. The tampon as claimed in claim 3, wherein each longitudinal rib, defined by the spiral longitudinal grooves, is separated from an adjacent longitudinal rib where they extend from the tampon core to an extent which is greater than that extent to which each said longitudinal rib is separated from such an adjacent longitudinal rib remotely from the tampon core.

10. The tampon as claimed in claim 9, wherein the spiral longitudinal grooves are closed, at least remotely from the tampon core.

11. The tampon as claimed in claim 10, wherein the separation of the ribs proximal the core cooperates with the closed portions of the grooves to form spiral liquid guide ducts.

12. The tampon as claimed in claim 11, wherein the liquid guide ducts are open at the insertion end and at the recovery end of the tampon.

13. The tampon as claimed in claim 1, wherein the insertion end of the tampon is provided with a round dome.

14. The tampon as claimed in claim 1, wherein the recovery end of the tampon is provided with a finger recess.

15. The tampon as claimed in claim 3, wherein the tampon has an approximately circular diameter of about 6 to about 17 mm and the tampon core has a diameter of up to about 5 mm.

16. The tampon as claimed in claim 1, wherein at least a portion of the outer circumferential surface of the tampon is smooth.

17. A tampon comprising a dimensionally stable, compressed fiber core and a flexible recovery element, the tampon is arranged and configured for digital insertion and has an insertion end, a recovery end, a longitudinal axis, and a substantially cylindrical outer surface, wherein the fiber core comprises fibrous material having a first density, and wherein longitudinal ribs extend radially outward from the fiber core, and wherein the longitudinal ribs define spirally shaped, longitudinal grooves on at least a portion of the outer surface, wherein the tampon has sufficient column strength to permit digital insertion thereof into a body cavity.

18. The tampon according to claim 17 wherein said longitudinal ribs comprise fibrous material having a second density less than the first density.

19. The tampon according to claim 17 wherein said longitudinal ribs extend radially outward at equal circumferential angle intervals and between the insertion end and the recovery end.

20. The tampon as claimed in claim 17, wherein a circumferential surface of fiber core is substantially cylindrical.

21. The tampon as claimed in claim 17, wherein the spiral longitudinal grooves each extend over a circumferential angle of up to at least 150° of the tampon.

22. The tampon as claimed in claim 21, wherein the circumferential angle is about 80° to about 120°.

23. The tampon as claimed in claim 17, wherein each longitudinal rib, defined by the spiral longitudinal grooves, is separated from an adjacent longitudinal rib where they extend from the compressed fiber core to an extent which is greater than that extent to which each said longitudinal rib is separated from such an adjacent longitudinal rib remotely from the compressed fiber core.

24. The tampon as claimed in claim 23, wherein the spiral longitudinal grooves are closed, at least remotely from the compressed fiber core.

25. The tampon as claimed in claim 24, wherein the separation of the ribs proximal the core cooperates with the closed portions of the grooves to form spiral liquid guide ducts.

26. The tampon as claimed in claim 25, wherein the liquid guide ducts are open at the insertion end and at the recovery end of the tampon.

27. The tampon as claimed in claim 17, wherein the tampon has an approximately circular diameter of about 6 mm to about 17 mm and the compressed fiber core has a diameter of up to about 5 mm.

28. The tampon as claimed in claim 17, wherein at least a portion of the outer circumferential surface of the tampon is smooth.

29. A tampon comprising:
a dimensionally stable, compressed fiber core, the tampon is arranged and configured for digital insertion and has an insertion end, a recovery end, a longitudinal axis, and a substantially cylindrical outer surface,
wherein the fiber core comprises fibrous material having a first density,
wherein longitudinal ribs extend radially outward from the fiber core,
wherein the longitudinal ribs define spirally shaped, longitudinal grooves on at least a portion of the outer surface,
wherein each longitudinal rib is separated from an adjacent longitudinal rib where they extend from the tampon core to an extent which is greater than that extent to which each said longitudinal rib is separated from such an adjacent longitudinal rib remotely from the tampon core, and
wherein the tampon has sufficient column strength to permit insertion thereof into a body cavity.

30. The tampon as claimed in claim 9, wherein the spiral longitudinal grooves are closed, at least remotely from the tampon core.

31. The tampon as claimed in claim 10, wherein the separation of the ribs proximal the core cooperates with the closed portions of the grooves to form spiral liquid guide ducts.

32. The tampon as claimed in claim 11, wherein the liquid guide ducts are open at the insertion end and at the recovery end of the tampon.

* * * * *